(12) United States Patent
Erickson et al.

(10) Patent No.: US 11,873,524 B2
(45) Date of Patent: Jan. 16, 2024

(54) METHODS AND SYSTEMS FOR THE RAPID DETECTION OF *SALMONELLA* USING INFECTIOUS AGENTS

(71) Applicant: Laboratory Corporation of America Holdings, Burlington, NC (US)

(72) Inventors: Stephen Erickson, White Bear Township, MN (US); Jose S. Gil, Winnetka, CA (US); Minh Mindy Bao Nguyen, Shoreview, MN (US); Dwight Lyman Anderson, Minneapolis, MN (US); Jessica Stach, St. Paul, MN (US)

(73) Assignee: Laboratory Corporation of America Holdings, Burlington, NC (US)

( * ) Notice: Subject to any disclaimer, the term of this patent is extended or adjusted under 35 U.S.C. 154(b) by 104 days.

(21) Appl. No.: 16/247,486

(22) Filed: Jan. 14, 2019

(65) Prior Publication Data

US 2019/0218589 A1    Jul. 18, 2019

Related U.S. Application Data

(60) Provisional application No. 62/661,739, filed on Apr. 24, 2018, provisional application No. 62/628,616, (Continued)

(51) Int. Cl.
*C12Q 1/10* (2006.01)
*C12N 15/86* (2006.01)
(Continued)

(52) U.S. Cl.
CPC ............... *C12Q 1/10* (2013.01); *A61K 35/76* (2013.01); *C12N 7/00* (2013.01); *C12N 15/65* (2013.01);
(Continued)

(58) Field of Classification Search
None
See application file for complete search history.

(56) References Cited

U.S. PATENT DOCUMENTS 5,824,468 A    10/1998   Scherer et al.
9,828,625 B2*  11/2017   Koeris ..................... C12N 7/00
(Continued)

FOREIGN PATENT DOCUMENTS

CN      101204584 A    6/2008
JP      2017511702 A   4/2017
(Continued)

OTHER PUBLICATIONS

Omiccioli E, Amagliani G, Brandi G, Magnani M. A new platform for Real-Time PCR detection of *Salmonella* spp., Listeria monocytogenes and *Escherichia coli* O157 in milk. Food Microbiol. Sep. 2009;26(6):615-22. doi: 10.1016/j.fm.2009.04.008. Epub May 3, 2009. PMID: 19527837. (Year: 2009).*
(Continued)

*Primary Examiner* — Michelle S Horning
(74) *Attorney, Agent, or Firm* — Kilpatrick Townsend & Stockton LLP

(57) ABSTRACT

Disclosed herein are methods and systems for rapid detection of microorganisms in a sample. A genetically modified bacteriophage is also disclosed which comprises an indicator gene in the late gene region. The specificity of the bacteriophage, such as *Salmonella*-specific bacteriophage, allows detection of a specific microorganism, such as *Salmonella* spp. and an indicator signal may be amplified to optimize assay sensitivity.

6 Claims, 8 Drawing Sheets

Related U.S. Application Data filed on Feb. 9, 2018, provisional application No. 62/616,956, filed on Jan. 12, 2018.

(51) Int. Cl.

| | |
|---|---|
| *C12N 15/65* | (2006.01) |
| *C12Q 1/70* | (2006.01) |
| *G01N 33/50* | (2006.01) |
| *C12Q 1/66* | (2006.01) |
| *A61K 35/76* | (2015.01) |
| *C12N 15/74* | (2006.01) |
| *C12N 7/00* | (2006.01) |
| *C12Q 1/6897* | (2018.01) |
| *C12Q 1/02* | (2006.01) |

(52) U.S. Cl.
CPC ............. *C12N 15/74* (2013.01); *C12N 15/86* (2013.01); *C12Q 1/025* (2013.01); *C12Q 1/66* (2013.01); *C12Q 1/6897* (2013.01); *C12Q 1/70* (2013.01); *G01N 33/50* (2013.01); *C12N 2795/00021* (2013.01); *C12N 2795/00031* (2013.01); *C12N 2795/00051* (2013.01); *C12N 2795/10131* (2013.01); *C12N 2795/10143* (2013.01); *C12Q 2304/60* (2013.01); *G01N 2800/52* (2013.01)

(56) References Cited

U.S. PATENT DOCUMENTS

| | | | |
|---|---|---|---|
| 10,519,483 B2* | 12/2019 | Anderson | ............ G01N 33/569 |
| 2015/0218616 A1 | 8/2015 | Anderson et al. | |
| 2017/0121688 A1 | 5/2017 | Gil et al. | |

FOREIGN PATENT DOCUMENTS

| | | |
|---|---|---|
| WO | 2017127434 | 7/2017 |
| WO | 2017/172644 A2 | 10/2017 |

OTHER PUBLICATIONS

Cao R, Zeaki N, Wallin-Carlquist N, Skandamis PN, Schelin J, Rådström P. Elevated enterotoxin A expression and formation in *Staphylococcus aureus* and its association with prophage induction. Appl Environ Microbiol. Jul. 2012;78(14):4942-8. doi: 10.1128/AEM.00803-12. Epub Apr. 27, 2012. (Year: 2012).*

Chen C, Bales P, Greenfield J, Heselpoth RD, Nelson DC, Herzberg O. Crystal structure of ORF210 from *E. coli* O157:H1 phage CBA120 (TSP1), a putative tailspike protein. PLoS One. Mar. 26, 2014;9(3):e93156. doi: 10.1371/journal.pone.0093156. PMID: 24671238; PMCID: PMC3966878. (Year: 2014).*

International Patent Application No. PCT/US2019/013543, International Preliminary Report on Patentability, dated Jul. 23, 2020, 9 pages.

Akhtar et al., "Isolation, Identification and Characterization of Lytic, Wide Host Range Bacteriophages From Waste Effluents Against *Salmonella enterica* Serovars", Food Control, vol. 38, No. 1, Apr. 1, 2014, pp. 67-74.

Goodridge et al., "Reporter Bacteriophage Assays as a Means to Detect Foodborne Pathogenic Bacteria", Food Research International, vol. 35, No. 9, Jan. 1, 2002, pp. 863-870.

PCT/US2019/013543 , "International Search Report and Written Opinion", dated Apr. 5, 2019, 15 pages.

CA 3083263, Office Action, dated May 25, 2021, 4 pages.

EP 19706782.0, Office Action, dated Apr. 7, 2022, 4 pages.

Kim, S. et al., "Development of an Engineered Bioluminescent Reporter Phage for the Sensitive Detection of Viable *Salmonella typhimurium*", J. Anal. Chem. 84:5858-5864 (2014).

Loessner, M. et al., "Organization and Transcriptional Analysis of the *Listeria* Phage A511 Late Gene Region Comprising the Major Capsid and Tail Sheath Protein Genes cps and tsh," J. Bacteriol. 177(2):6601-6609 (1995).

CA 3083263, Office Action, dated May 18, 2022, 4 pages.

JP 2020-538026, Office Action, dated Dec. 7, 2022, 13 pages.

Canadian Application No. 3083263, Office Action dated Jul. 6, 2023, 4 pages.

Cahill et al., Powdered Infant Formula as a Source of *Salmonella* Infection in Infants, Clinical Infectious Diseases, vol. 46, No. 2, Jan. 15, 2008, pp. 268-273.

Chinese Application No. 201980007575.7, Office Action dated Mar. 24, 2023, 24 pages (11 pages of Original Document and 13 pages of English Translation).

European Application No. 19706782.0, Office Action dated Jun. 29, 2023, 6 pages.

Japanese Application No. 2020-538026, Office Action dated Aug. 8, 2023, 13 pages (4 pages of Original Document and 9 pages of English Translation).

Wall et al., Targeting Tumors with *Salmonella* Typhimurium-Potential for Therapy, Oncotarget, vol. 1, No. 8, Dec. 2010, pp. 721-728.

\* cited by examiner

METHODS AND SYSTEMS FOR THE RAPID DETECTION OF *SALMONELLA* USING INFECTIOUS AGENTS

CROSS REFERENCE TO RELATED APPLICATION

The present application claims priority to U.S. provisional Application Nos. 62/616,956, filed on Jan. 12, 2018; 62/628,616, filed on Feb. 9, 2018; and 62/661,739, filed on Apr. 24, 2019. The disclosures of U.S. application Ser. Nos. 13/773,339, 14/625,481, 15/263,619, 15/409,258 and U.S. provisional Application Nos. 62/616,956, 62/628,616, and 62/661,739 are hereby incorporated by reference in their entirety herein.

FIELD OF THE INVENTION

This invention relates to compositions, methods, systems, and kits for the detection of microorganisms using infectious agents.

BACKGROUND

There is a strong interest in improving speed and sensitivity for detection of bacteria, viruses, and other microorganisms in biological, food, water, and clinical samples. Microbial pathogens can cause substantial morbidity among humans and domestic animals, as well as immense economic loss. Also, detection of microorganisms is a high priority for the Food and Drug Administration (FDA), United States Department of Agriculture (USDA), and Centers for Disease Control (CDC) given outbreaks of life-threatening or fatal illness caused by ingestion of food contaminated with certain microorganisms, e.g., *Salmonella* spp.

Traditional microbiological tests for the detection of bacteria rely on non-selective and selective enrichment cultures followed by plating on selective media and further testing to confirm suspect colonies. Such procedures can require several days. A variety of rapid methods have been investigated and introduced into practice to reduce the time requirement. However, these methods have drawbacks. For example, techniques involving direct immunoassays or gene probes generally require an overnight enrichment step in order to obtain adequate sensitivity. Polymerase chain reaction (PCR) tests also include an amplification step and therefore are capable of both very high sensitivity and selectivity; however, the sample size that can be economically subjected to PCR testing is limited. With dilute bacterial suspensions, most small sub samples will be free of cells and therefore purification and/or lengthy enrichment steps are still required.

The time required for traditional biological enrichment is dictated by the growth rate of the target bacterial population of the sample, by the effect of the sample matrix, and by the required sensitivity. In practice, most high sensitivity methods employ an overnight incubation and take about 24 hours overall. Due to the time required for cultivation, these methods can take up to three days, depending upon the organism to be identified and the source of the sample. This lag time is generally unsuitable as the contaminated food, water, or other product may have already made its way into livestock or humans. In addition, increases in antibiotic-resistant bacteria and biodefense considerations make rapid identification of bacterial pathogens in water, food and clinical samples critical priorities worldwide.

Therefore, there is a need for more rapid, simple, and sensitive detection and identification of microorganisms, such as bacteria and other potentially pathogenic microorganisms.

SUMMARY

Embodiments of the invention comprise compositions, methods, systems, and kits for the detection of microorganisms of interest, such as *Salmonella* spp. The invention may be embodied in a variety of ways.

In some aspects, the invention comprises a recombinant bacteriophage comprising an indicator gene inserted into a late gene region of a bacteriophage genome. In some embodiments the recombinant bacteriophage is a genetically modified *Salmonella*-specific bacteriophage genome. In certain embodiments the recombinant bacteriophage is a genetically modified bacteriophage genome. In some embodiments, the bacteriophage used to prepare the recombinant bacteriophage specifically infects *Salmonella* spp. In an embodiment, the recombinant bacteriophage can distinguish *Salmonella* spp. in the presence of other types of bacteria.

In some embodiments of recombinant indicator bacteriophage, the indicator gene can be codon-optimized and can encode a soluble protein product that generates an intrinsic signal or a soluble enzyme that generates signal upon reaction with substrate. Some recombinant bacteriophage further comprise an untranslated region upstream of a codon-optimized indicator gene, wherein the untranslated region includes a bacteriophage late gene promoter and a ribosomal entry site. In some embodiments, the indicator gene is a luciferase gene. The luciferase gene can be a naturally occurring gene, such as Oplophorus luciferase, Firefly luciferase, Lucia luciferase, or Renilla luciferase, or it can be a genetically engineered gene such as NANOLUC®.

Also disclosed herein are methods for preparing a recombinant indicator bacteriophage. Some embodiments include selecting a wild-type bacteriophage that specifically infects a target pathogenic bacterium; preparing a homologous recombination plasmid/vector comprising an indicator gene; transforming the homologous recombination plasmid/vector into target pathogenic bacteria; infecting the transformed target pathogenic bacteria with the selected wild-type bacteriophage, thereby allowing homologous recombination to occur between the plasmid/vector and the bacteriophage genome; and isolating a particular clone of recombinant bacteriophage. In some embodiments the selected wild-type bacteriophage is a *Salmonella*-specific bacteriophage. In some embodiments, the selected wild-type bacteriophage is a myovirus, such as T4, T4-like, or Vil-like. In other embodiments, the selected wild-type bacteriophage is a siphovirus, such as T5likevirus. In other embodiments, the selected wild-type bacteriophage is TSP1 or TSP11. TSP1 and TSP11 are newly isolated and sequenced phages, respectively, likely myovirus related to T4 phage and siphovirus related to or within the T5likevirus genus. In still other embodiments, the bacteriophage are the *Salmonella*-specific bacteriophage SEA1 and TSP1.

In some embodiments, preparing a homologous recombination plasmid/vector includes determining the natural nucleotide sequence in the late region of the genome of the selected bacteriophage; annotating the genome and identifying the major capsid protein gene of the selected bacteriophage; designing a sequence for homologous recombination downstream of the major capsid protein gene, wherein the sequence comprises a codon-optimized indicator gene;

and incorporating the sequence designed for homologous recombination into a plasmid/vector. The step of designing a sequence can include inserting a genetic construct comprising, an untranslated region, including a phage late gene promoter and ribosomal entry site, upstream of the codon-optimized indicator gene. In some embodiments, the phage late gene promoter is an exogenous promoter, different from any endogenous promoter in the phage genome. Thus, in some methods, the homologous recombination plasmid comprises an untranslated region including a bacteriophage late gene promoter and a ribosomal entry site upstream of the codon-optimized indicator gene.

Some embodiments of the invention are compositions that include a recombinant indicator bacteriophage as described herein. For example, compositions can include one or more wild-type or genetically modified infectious agents (e.g., bacteriophages) and one or more indicator genes. In some embodiments, compositions can include cocktails of different indicator phages that may encode and express the same or different indicator proteins.

In some embodiments, the invention comprises a method for detecting a microorganism of interest in a sample comprising the steps of incubating the sample with a recombinant bacteriophage that infects the microorganism of interest, wherein the recombinant bacteriophage comprises an indicator gene inserted into a late gene region of the bacteriophage such that expression of the indicator gene during bacteriophage replication following infection of host bacteria results in a soluble indicator protein product, and detecting the indicator protein product, wherein positive detection of the indicator protein product indicates that the microorganism of interest is present in the sample.

In some embodiments of methods for preparing recombinant indicator bacteriophage, the wild-type bacteriophage is a *Salmonella*-specific bacteriophage and the target pathogenic bacteria are *Salmonella* spp. In some embodiments, isolating a particular clone of recombinant bacteriophage comprises a limiting dilution assay for isolating a clone that demonstrates expression of the indicator gene.

Other aspects of the invention include methods for detecting bacteria, such as *Salmonella* spp. in a sample, including steps of incubating the sample with a recombinant bacteriophage derived from *Salmonella*-specific bacteriophage and detecting an indicator protein product produced by the recombinant bacteriophage, wherein positive detection of the indicator protein product indicates that *Salmonella* spp. is present in the sample. The sample can be a food, environmental, water, commercial, or clinical sample.

In some embodiments of methods for detecting bacteria, the sample is first incubated in conditions favoring growth for an enrichment period of 24 hours or less, 23 hours or less, 22 hours or less, 21 hours or less, 20 hours or less, 19 hours or less, 18 hours or less, 17 hours or less, 16 hours or less, 15 hours or less, 14 hours or less, 13 hours or less, 12 hours or less, 11 hours or less, 10 hours or less, or 9 hours or less, 8 hours or less, 7 hours or less, 6 hours or less, 5 hours or less, 4 hours or less, 3 hours or less, or 2 hours or less. In some embodiments, the sample is not enriched prior to detection. In some embodiments, the total time to results is less than 26 hours, less than 25 hours, less than 24 hours, less than 23 hours, less than 22 hours, less than 21 hours, less than 20 hours, less than 19 hours, less than 18 hours, less than 17 hours, less than 16 hours, less than 15 hours, less than 14 hours, less than 13 hours, less than 12 hours, less than 11 hours, less than 10 hours, less than 9 hours, less than 8 hours, less than 7 hours, less than 6 hours, less than 5 hours, or less than 4 hours. In some embodiments, the ratio of signal to background generated by detecting the indicator is at least 2.0 or at least 2.5. In some embodiments, the method detects as few as 1, 2, 3, 4, 5, 6, 7, 8, 9, 10, 15, 20, 30, 40, 50, 60, 70, 80, 90, or 100 of the specific bacteria in a sample of a standard size for the food safety industry.

Additional embodiments include systems and kits for detecting *Salmonella* spp., wherein the systems or kits include a recombinant bacteriophage derived from *Salmonella*-specific bacteriophage. Some embodiments further include a substrate for reacting with an indicator to detect the soluble protein product expressed by the recombinant bacteriophage. These systems or kits can include features described for the bacteriophage, compositions, and methods of the invention. In still other embodiments, the invention comprises non-transient computer readable media for use with methods or systems according to the invention.

BRIEF DESCRIPTION OF THE FIGURES

The present invention may be better understood by referring to the following non-limiting figures.

DETAILED DESCRIPTION OF THE INVENTION

Figure 1:
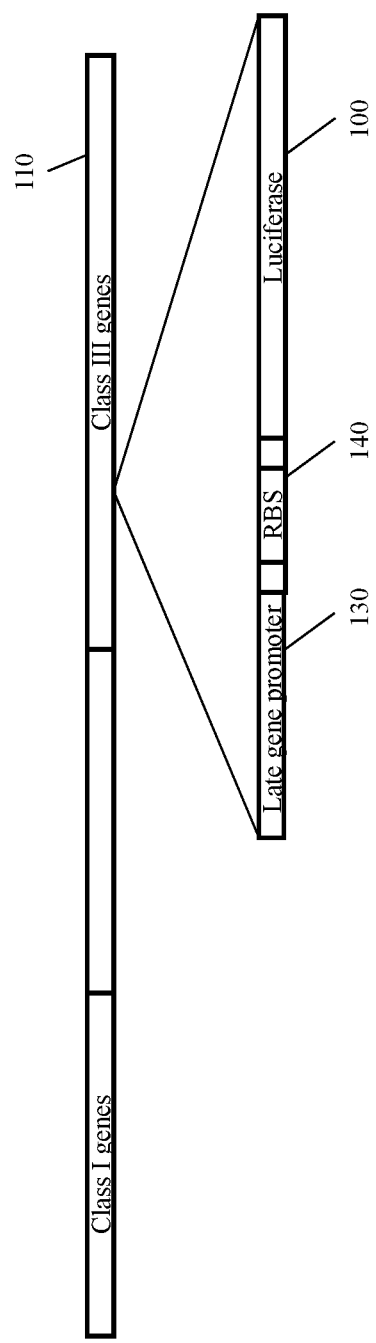
FIG. 1 depicts an indicator phage construct according to an embodiment of the invention illustrating insertion of a genetic construct comprising a luciferase gene, and a T4-like late promoter, and a ribosomal binding site (RBS) inserted into the late (class III) region of a bacteriophage. The promoter depicted is in addition to and separate from the endogenous late gene promoter upstream of the endogenous late genes, such as the gene for major capsid protein (MCP).

Disclosed herein are compositions, methods and systems that demonstrate surprising sensitivity for detection of microorganisms of interest, such as *Salmonella* spp., in test samples (e.g., biological, food, water, environmental, and clinical samples). Detection can be achieved in a shorter timeframe than was previously thought possible using genetically modified infectious agents in assays performed without culturing for enrichment, or in some embodiments with minimal incubation times during which microorganisms could potentially multiply. Also surprising is the success of using a potentially high multiplicity of infection (MOI), or high concentrations of plaque forming units (PFU), for incubation with a test sample. Such high phage concentrations (PFU/mL) were previously purported to be detrimental in bacterium detection assays, as they were purported to cause "lysis from without." However, a high concentration of phage can facilitate finding, binding, and infecting a low number of target cells.

The compositions, methods, systems and kits of the invention may comprise infectious agents for use in detection of such microorganisms, including *Salmonella* spp. In certain embodiments, the invention may comprise a composition comprising a recombinant bacteriophage having an indicator gene inserted into a late gene region of the bacteriophage. In certain embodiments, expression of the indicator gene during bacteriophage replication following infection of a host bacterium results in production of a soluble indicator protein product. In certain embodiments, the indicator gene may be inserted into a late gene (i.e., class III) region of the bacteriophage. The bacteriophage can be derived from podoviruses such as T7, T7-like, myoviruses such as T4, T4-like, ViI, ViI-like (or Vi1 virus, per GenBank/NCBI), *Salmonella*-specific bacteriophage, or another wild-type or engineered bacteriophage.

In some aspects, the invention comprises a method for detecting a microorganism of interest. The method may use an infectious agent for detection of the microorganism of interest. For example, in certain embodiments, the microorganism of interest is a bacterium, such as *Salmonella* spp., and the infectious agent is a bacteriophage. Thus, in certain embodiments, the method may comprise detection of a bacterium of interest in a sample by incubating the sample with a recombinant bacteriophage that infects the bacterium of interest. In certain embodiments, the recombinant bacteriophage comprises an indicator gene. The indicator gene may, in certain embodiments, be inserted into a late gene region of the bacteriophage such that expression of the indicator gene during bacteriophage replication following infection of host bacteria results in production of an indicator protein product. The method may comprise detecting the indicator protein product, wherein positive detection of the indicator protein product indicates that the bacterium of interest is present in the sample. In some embodiment the indicator protein is soluble.

In certain embodiments, the invention may comprise a system. The system may contain at least some of the compositions of the invention. Also, the system may comprise at least some of the components for performing the method. In certain embodiments, the system is formulated as a kit. Thus, in certain embodiments, the invention may comprise a system for rapid detection of a microorganism of interest, such as *Salmonella* spp., in a sample, comprising: a component for incubating the sample with an infectious agent specific for the microorganism of interest, wherein the infectious agent comprises an indicator moiety; and a component for detecting the indicator moiety. In yet other embodiments, the invention comprises software for use with the methods or systems.

Thus, some embodiments of the present invention solve a need by using bacteriophage-based methods for amplifying a detectable signal indicating the presence of bacteria. In certain embodiments as little as a single bacterium is detected. The principles applied herein can be applied to the detection of a variety of microorganisms. Because of numerous binding sites for an infectious agent on the surface of a microorganism, the capacity to produce one hundred or more agent progeny during infection, and the potential for high level expression of an encoded indicator moiety, the infectious agent or an indicator moiety can be more readily detectable than the microorganism itself. In this way, embodiments of the present invention can achieve tremendous signal amplification from even a single infected cell.

Aspects of the present invention utilize the high specificity of binding agents that can bind to particular microorganisms, such as the binding component of infectious agents, as a means to detect and/or quantify the specific microorganism in a sample. In some embodiments, the present invention utilizes the high specificity of infectious agents such as bacteriophage.

In some embodiments, detection is achieved through an indicator moiety associated with the binding agent specific for the microorganism of interest. For example, an infectious agent may comprise an indicator moiety, such as a gene encoding a soluble indicator. In some embodiments the indicator may be encoded by the infectious agent, such as a bacteriophage, and the bacteriophage is designated an indicator phage.

Some embodiments of the invention disclosed and described herein utilize the discovery that a single microorganism is capable of binding specific recognition agents, such as phage. Following infection and replication of the phage, progeny phage may be detected via an indicator moiety expressed during phage replication. This principle allows amplification of indicator signal from one or a few cells based on specific recognition of microorganism surface receptors. For example, by exposing even a single cell of a bacterium to a plurality of phage, thereafter allowing amplification of the phage and high-level expression of an encoded indicator gene product during replication, the indicator signal is amplified such that the single bacterium is detectable.

Embodiments of the methods and systems of the invention can be applied to detection and quantification of a variety of microorganisms (e.g., bacteria) in a variety of circumstances, including but not limited to detection of pathogens from food, water, clinical, environmental, and commercial samples. In some embodiments, clinical samples can be analyzed for the presence of microorganisms. The methods of the present invention provide high detection sensitivity and specificity rapidly. In some embodiments detection is possible within a single replication cycle of the bacteriophage, which is unexpected.

Definitions

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well-known and commonly used in the art. Known methods and techniques are generally performed according to conventional methods well known in the art and as described in various general and more specific references that are discussed throughout the present specification unless otherwise indicated. Enzymatic reactions and purification techniques are performed according to manufacturer's specifications, as commonly accomplished in the art or as described herein. The nomenclatures used in connection with the laboratory procedures and techniques described herein are those well-known and commonly used in the art.

The following terms, unless otherwise indicated, shall be understood to have the following meanings:

As used herein, the terms "a", "an", and "the" can refer to one or more unless specifically noted otherwise.

The use of the term "or" is used to mean "and/or" unless explicitly indicated to refer to alternatives only or the alternatives are mutually exclusive, although the disclosure supports a definition that refers to only alternatives and "and/or." As used herein "another" can mean at least a second or more.

Throughout this application, the term "about" is used to indicate that a value includes the inherent variation of error for the device, the method being employed to determine the value, or the variation that exists among samples.

The term "solid support" or "support" means a structure that provides a substrate and/or surface onto which biomolecules may be bound. For example, a solid support may be an assay well (i.e., such as a microtiter plate or multi-well plate), or the solid support may be a location on a filter, an array, or a mobile support, such as a bead or a membrane (e.g., a filter plate, lateral flow strip, latex particles, or paramagnetic particles).

The term "binding agent" refers to a molecule that can specifically and selectively bind to a second (i.e., different) molecule of interest. The interaction may be non-covalent, for example, as a result of hydrogen bonding, van der Waals interactions, or electrostatic or hydrophobic interactions, or it may be covalent. The term "soluble binding agent" refers to a binding agent that is not associated with (i.e., covalently or non-covalently bound) to a solid support.

As used herein, an "analyte" refers to a molecule, compound or cell that is being measured. The analyte of interest may, in certain embodiments, interact with a binding agent. As described herein, the term "analyte" may refer to a protein or peptide of interest. An analyte may be an agonist, an antagonist, or a modulator. Or, an analyte may not have a biological effect. Analytes may include small molecules, sugars, oligosaccharides, lipids, peptides, peptidomimetics, organic compounds and the like.

The term "detectable moiety" or "detectable biomolecule" or "reporter" or "indicator" or "indicator moiety" refers to a molecule that can be measured in a quantitative assay. For example, an indicator moiety may comprise an enzyme that may be used to convert a substrate to a product that can be measured. An indicator moiety may be an enzyme that catalyzes a reaction that generates bioluminescent emissions (e.g., luciferase). Or, an indicator moiety may be a radioisotope that can be quantified. Or, an indicator moiety may be a fluorophore. Or, other detectable molecules may be used.

As used herein, "bacteriophage" or "phage" includes one or more of a plurality of bacterial viruses. In this disclosure, the terms "bacteriophage" and "phage" include viruses such as mycobacteriophage (such as for TB and paraTB), mycophage (such as for fungi), mycoplasma phage, and any other term that refers to a virus that can invade living bacteria, fungi, mycoplasma, protozoa, yeasts, and other microscopic living organisms and uses them to replicate itself. Here, "microscopic" means that the largest dimension is one millimeter or less. Bacteriophages are viruses that have evolved in nature to use bacteria as a means of replicating themselves. A phage does this by attaching itself to a bacterium and injecting its DNA (or RNA) into that bacterium, and inducing it to replicate the phage hundreds or even thousands of times. This is referred to as phage amplification.

As used herein, "late gene region" refers to a region of a viral genome that is transcribed late in the viral life cycle. The late gene region typically includes the most abundantly expressed genes (e.g., structural proteins assembled into the bacteriophage particle). Late genes are synonymous with class III genes and include genes with structure and assembly functions. For example, the late genes (synonymous with class III) are transcribed in phage T7, e.g., from 8 minutes after infection until lysis, class I (e.g., RNA polymerase) is early from 4-8 minutes, and class II from 6-15 minutes, so there is overlap in timing of II and III. A late promoter is one that is naturally located and active in such a late gene region.

As used herein, "culturing for enrichment" refers to traditional culturing, such as incubation in media favorable to propagation of microorganisms, and should not be confused with other possible uses of the word "enrichment," such as enrichment by removing the liquid component of a sample to concentrate the microorganism contained therein, or other forms of enrichment that do not include traditional facilitation of microorganism propagation. Culturing for enrichment for a period of time may be employed in some embodiments of methods described herein, but is not necessary and is for a much shorter period of time than traditional culturing for enrichment.

As used herein "recombinant" refers to genetic (i.e., nucleic acid) modifications as usually performed in a laboratory to bring together genetic material that would not otherwise be found. This term is used interchangeably with the term "modified" herein.

As used herein "RLU" refers to relative light units as measured by a luminometer (e.g., GLOMAX® 96) or similar instrument that detects light. For example, the detection of the reaction between luciferase and appropriate substrate (e.g., NANOLUC® with NANO-GLO®) is often reported in RLU detected.

As used herein "time to results" refers to the total amount of time from beginning of sample incubation to generated result. Time to results does not include any confirmatory testing time. Data collection can be done at any time after a result has been generated.

Samples

Each of the embodiments of the methods and systems of the invention can allow for the rapid detection and quantification of microbes in a sample. For example, methods according to the present invention can be performed in a shortened time period with superior results.

Microbes detected by the methods and systems of the present invention include pathogens that are of natural, commercial, medical or veterinary concern. Such pathogens include Gram-negative bacteria or Gram-positive bacteria. Any microbe for which an infectious agent that is specific for the particular microbe has been identified can be detected by the methods of the present invention. Those skilled in the art will appreciate that there is no limit to the application of the present methods other than the availability of the necessary specific infectious agent/microbe pairs.

Bacterial cells detectable by the present invention include, but are not limited to, bacterial cells that are food or water-borne pathogens. In some embodiments, bacterial cells detectable by the present invention include antibiotic-resistant bacteria (e.g., antibiotic-resistant *Salmonella*).

The sample may be an environmental or food or water sample. Some embodiments may include medical or veterinary samples. Samples may be liquid, solid, or semi-solid. Samples may be swabs of solid surfaces. Samples may include environmental materials, such as the water samples, or the filters from air samples or aerosol samples from cyclone collectors. Samples include but are not limited to, pet food, dog food, vegetables, meat, fish, poultry, peanut butter, processed foods, powdered infant formula, powdered milk, teas, starches, eggs, milk, cheese, other dairy products, processed or unprocessed foods, ready-to-eat (RTE) foods, dried foods, or spices. Medical or veterinary samples include, but are not limited to, blood, sputum, cerebrospinal fluid, and fecal samples and different types of swabs.

In some embodiments, samples may be used directly in the detection methods of the present invention, without preparation, concentration, or dilution. For example, liquid samples, including but not limited to, milk and juices, may be assayed directly. Samples may be diluted or suspended in solution, which may include, but is not limited to, a buffered solution or a bacterial culture medium. A sample that is a solid or semi-solid may be suspending in a liquid by mincing, mixing or macerating the solid in the liquid. A sample should be maintained within a pH range that promotes bacteriophage attachment to the host bacterial cell. A sample should also contain the appropriate concentrations of divalent and monovalent cations, including but not limited to $Na^+$, $Mg^+$, and $Ca^+$. Preferably a sample is maintained at a temperature that maintains the viability of any pathogen cells contained within the sample.

In some embodiments of the detection assay, the sample is maintained at a temperature that maintains the viability of any pathogen cell present in the sample. For example, during steps in which bacteriophages are attaching to bacterial cells, it is preferable to maintain the sample at a temperature that facilitates bacteriophage attachment. During steps in which bacteriophages are replicating within an infected bacterial cell or lysing such an infected cell, it is preferable to maintain the sample at a temperature that promotes bacteriophage replication and lysis of the host. Such temperatures are at least about 25 degrees Celsius (C), more preferably no greater than about 45 degrees C., most preferably about 37 degrees C.

Assays may include various appropriate control samples. For example, control samples containing no bacteriophages or control samples containing bacteriophages without bacteria may be assayed as controls for background signal levels.

Indicator Bacteriophage

As described in more detail herein, the compositions, methods, systems and kits of the invention may comprise infectious agents for use in detection of pathogenic microorganisms. In certain embodiments, the invention comprises a recombinant indicator bacteriophage, wherein the bacteriophage genome is genetically modified to include an indicator or reporter gene. In some embodiments, the invention may include a composition comprising a recombinant bacteriophage having an indicator gene incorporated into the genome of the bacteriophage.

A recombinant indicator bacteriophage can include a reporter or indicator gene. In certain embodiments of the infectious agent, the indicator gene does not encode a fusion protein. For example, in certain embodiments, expression of the indicator gene during bacteriophage replication following infection of a host bacterium results in a soluble indicator protein product. In certain embodiments, the indicator gene may be inserted into a late gene region of the bacteriophage. Late genes are generally expressed at higher levels than other phage genes, as they code for structural proteins. The late gene region may be a class III gene region and may include a gene for a major capsid protein.

Some embodiments include designing (and optionally preparing) a sequence for homologous recombination downstream of the major capsid protein gene. Other embodiments include designing (and optionally preparing) a sequence for homologous recombination upstream of the major capsid protein gene. In some embodiments, the sequence comprises a codon-optimized reporter gene preceded by an untranslated region. The untranslated region may include a phage late gene promoter and ribosomal entry site.

In some embodiments, an indicator bacteriophage is derived from T7, T5, T4 or another similar phage. An indicator bacteriophage may also be derived from T4-like, T5-like, T7-like, ViI, ViI-like, *Salmonella*-specific bacteriophage, or another bacteriophage having a genome with at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% homology to T7, T7-like, T5, T5-like, T4, T4-like, *Salmonella*-specific bacteriophage, ViI, or ViI-like (or ViI virus-like, per GenBank/NCBI) bacteriophages. In some embodiments, the indicator phage is derived from a bacteriophage that is highly specific for a particular pathogenic microorganism. The genetic modifications may avoid deletions of wild-type genes and thus the modified phage may remain more similar to the wild-type infectious agent than many commercially available phage. Environmentally derived bacteriophage may be more specific for bacteria that are found in the environment and as such, genetically distinct from phage available commercially.

Moreover, phage genes thought to be nonessential may have unrecognized function. For example, an apparently nonessential gene may have an important function in elevating burst size such as subtle cutting, fitting, or trimming functions in assembly. Therefore, deleting genes to insert an indicator may be detrimental. Most phages can package DNA that is a few percent larger than their natural genome. With this consideration, a smaller indicator gene may be a more appropriate choice for modifying a bacteriophage, especially one with a smaller genome. OpLuc and NANO-LUC® proteins are only about 20 kDa (approximately 500-600 bp to encode), while FLuc is about 62 kDa (approximately 1,700 bp to encode). For comparison, the genome of T7 is around 40 kbp, while the T4 genome is about 170 kbp, and the genome of *Salmonella* phage SEA1 bacteriophage is about 157 kbp. Moreover, the reporter gene should not be expressed endogenously by the bacteria (i.e., is not part of the bacterial genome), should generate a high signal to background ratio, and should be readily detectable in a timely manner. Promega's NANOLUC® is a modified Oplophorus gracilirostris (deep sea shrimp) luciferase. In some embodiments, NANOLUC® combined with Promega's NANO-GLO®, an imidazopyrazinone substrate (furimazine), can provide a robust signal with low background.

In some indicator phage embodiments, the indicator gene can be inserted into an untranslated region to avoid disruption of functional genes, leaving wild-type phage genes intact, which may lead to greater fitness when infecting non-laboratory strains of bacteria. Additionally, including stop codons in all three reading frames may help to increase expression by reducing read-through, also known as leaky expression. This strategy may also eliminate the possibility of a fusion protein being made at low levels, which would manifest as background signal (e.g., luciferase) that cannot be separated from the phage.

An indicator gene may express a variety of biomolecules. The indicator gene is a gene that expresses a detectable product or an enzyme that produces a detectable product. For example, in one embodiment the indicator gene encodes a luciferase enzyme. Various types of luciferase may be used. In alternate embodiments, and as described in more detail herein, the luciferase is one of Oplophorus luciferase, Firefly luciferase, Lucia luciferase, Renilla luciferase, or an engineered luciferase. In some embodiments, the luciferase gene is derived from Oplophorus. In some embodiments, the indicator gene is a genetically modified luciferase gene, such as NANOLUC®.

Thus, in some embodiments, the present invention comprises a genetically modified bacteriophage comprising a non-bacteriophage indicator gene in the late (class III) gene region. In some embodiments, the non-native indicator gene is under the control of a late promoter. Using a viral late gene promoter insures the reporter gene (e.g., luciferase) is not only expressed at high levels, like viral capsid proteins, but also does not shut down like endogenous bacterial genes or even early viral genes.

In some embodiments, the late promoter is a T4-, T5-, T7-, or ViI-like promoter, or another phage promoter similar to that found in the selected wild-type phage, i.e., without genetic modification. The late gene region may be a class III gene region, and the bacteriophage may be derived from T7, T5, T5-like, T4, T4-like, ViI, ViI-like, *Salmonella*-specific bacteriophage, or another natural bacteriophage having a genome with at least 70, 75, 80, 85, 90 or 95% homology to T7, T5, T5-like, T4, T4-like, ViI, ViI-like, or *Salmonella*-specific bacteriophage.

Genetic modifications to infectious agents may include insertions, deletions, or substitutions of a small fragment of nucleic acid, a substantial part of a gene, or an entire gene. In some embodiments, inserted or substituted nucleic acids comprise non-native sequences. A non-native indicator gene may be inserted into a bacteriophage genome such that it is under the control of a bacteriophage promoter. Thus, in some embodiments, the non-native indicator gene is not part of a fusion protein. That is, in some embodiments, a genetic modification may be configured such that the indicator protein product does not comprise polypeptides of the wild-type bacteriophage. In some embodiments, the indicator protein product is soluble. In some embodiments, the invention comprises a method for detecting a bacterium of interest comprising the step of incubating a test sample with such a recombinant bacteriophage.

In some embodiments, expression of the indicator gene in progeny bacteriophage following infection of host bacteria results in a free, soluble protein product. In some embodiments, the non-native indicator gene is not contiguous with a gene encoding a structural phage protein and therefore does not yield a fusion protein. Unlike systems that employ a fusion of a detection moiety to the capsid protein (i.e., a fusion protein), some embodiments of the present invention express a soluble indicator or reporter (e.g., soluble luciferase). In some embodiments, the indicator or reporter is ideally free of the bacteriophage structure. That is, the indicator or reporter is not attached to the phage structure. As such, the gene for the indicator or reporter is not fused with other genes in the recombinant phage genome. This may greatly increase the sensitivity of the assay (down to a single bacterium), and simplify the assay, allowing the assay to be completed in two hours or less or one hour or less for some embodiments, as opposed to several hours due to additional purification steps required with constructs that produce detectable fusion proteins. Further, fusion proteins may be less active than soluble proteins due, e.g., to protein folding constraints that may alter the conformation of the enzyme active site or access to the substrate.

Moreover, fusion proteins by definition limit the number of the moieties attached to subunits of a protein in the bacteriophage. For example, using a commercially available system designed to serve as a platform for a fusion protein would result in about 415 copies of the fusion moiety, corresponding to the about 415 copies of the gene 10B capsid protein in each T7 bacteriophage particle. Without this constraint, infected bacteria can be expected to express many more copies of the detection moiety (e.g., luciferase) than can fit on the bacteriophage. Additionally, large fusion proteins, such as a capsid-luciferase fusion, may inhibit assembly of the bacteriophage particle, thus yielding fewer bacteriophage progeny. Thus a soluble, non-fusion indicator gene product may be preferable.

In some embodiments, the indicator phage encodes a reporter, such as a detectable enzyme. The indicator gene product may generate light and/or may be detectable by a color change. Various appropriate enzymes are commercially available, such as alkaline phosphatase (AP), horseradish peroxidase (HRP), or luciferase (Luc). In some embodiments, these enzymes may serve as the indicator moiety. In some embodiments, Firefly luciferase is the indicator moiety. In some embodiments, Oplophorus luciferase is the indicator moiety. In some embodiments, NANOLUC® is the indicator moiety. Other engineered luciferases or other enzymes that generate detectable signals may also be appropriate indicator moieties.

In some embodiments, the use of a soluble detection moiety eliminates the need to remove contaminating parental phage from the lysate of the infected sample cells. With a fusion protein system, any bacteriophage used to infect sample cells would have the detection moiety attached, and would be indistinguishable from the daughter bacteriophage also containing the detection moiety. As detection of sample bacteria relies on the detection of a newly created (de novo synthesized) detection moiety, using fusion constructs requires additional steps to separate old (parental) moieties from newly created (daughter bacteriophage) moieties. This may be accomplished by washing the infected cells multiple times, prior to the completion of the bacteriophage life cycle, inactivating excess parental phage after infection by physical or chemical means, and/or chemically modifying the parental bacteriophage with a binding moiety (such as biotin), which can then be bound and separated (such as by streptavidin-coated sepharose beads). However, even with all these attempts at removal, parental phage can remain when a high concentration of parental phage is used to assure infection of a low number of sample cells, creating background signal that may obscure detection of signal from infected cell progeny phage.

By contrast, with the soluble detection moiety expressed in some embodiments of the present invention, purification of the parental phage from the final lysate is unnecessary, as the parental phage do not have any detection moiety attached. Thus any detection moiety present after infection must have been created de novo, indicating the presence of an infected bacterium or bacteria. To take advantage of this benefit, the production and preparation of parental phage may include purification of the phage from any free detection moiety produced during the production of parental bacteriophage in bacterial culture. Standard bacteriophage purification techniques may be employed to purify some embodiments of phage according to the present invention, such as sucrose density gradient centrifugation, cesium chloride isopycnic density gradient centrifugation, HPLC, size exclusion chromatography, and dialysis or derived technologies (such as Amicon brand concentrators—Millipore, Inc.). Cesium chloride isopycnic ultracentrifugation can be employed as part of the preparation of recombinant phage of the invention, to separate parental phage particles from contaminating luciferase protein produced upon propagation of the phage in the bacterial host. In this way, the parental recombinant bacteriophage of the invention is substantially free of any luciferase generated during production in the bacteria. Removal of residual luciferase present in the phage stock can substantially reduce background signal observed when the recombinant bacteriophage are incubated with a test sample.

In some embodiments of modified bacteriophage, the late promoter (class III promoter, e.g., from T7, T5, T4, ViI) has high affinity for RNA polymerase of the same bacteriophage that transcribes genes for structural proteins assembled into the bacteriophage particle. These proteins are the most abundant proteins made by the phage, as each bacteriophage particle comprises dozens or hundreds of copies of these molecules. The use of a viral late promoter can ensure optimally high level of expression of the luciferase detection moiety. The use of a late viral promoter derived from, specific to, or active under the original wild-type bacteriophage the indicator phage is derived from (e.g., a T4, T4-like, T5, T5-like, T7, ViI TSP1, SEA1 or TSP11) can further ensure optimal expression of the detection moiety. The use of a standard bacterial (non-viral/non-bacteriophage) promoter may in some cases be detrimental to expression, as these promoters are often down-regulated during bacteriophage infection (in order for the bacteriophage to prioritize the bacterial resources for phage protein production). Thus, in some embodiments, the phage is preferably engineered to encode and express at high level a soluble (free) indicator moiety, using a placement in the genome that does not limit expression to the number of subunits of a phage structural component.

Compositions of the invention may comprise one or more wild-type or genetically modified infectious agents (e.g., bacteriophages) and one or more indicator genes. In some embodiments, compositions can include cocktails of different indicator phages that may encode and express the same or different indicator proteins. In some embodiments, the cocktail of bacteriophage comprises at least two different types of recombinant bacteriophages.

Methods of Preparing Indicator Bacteriophage

Embodiments of methods for making indicator bacteriophage begin with selection of a wild-type bacteriophage for genetic modification. Some bacteriophage are highly specific for a target bacterium. This presents an opportunity for highly specific detection.

Thus, the methods of the present invention utilize the high specificity of binding agents, associated with infectious agents, that recognize and bind to a particular microorganism of interest as a means to amplify a signal and thereby detect low levels of a microorganism (e.g., a single microorganism) present in a sample. For example, infectious agents (e.g., bacteriophage) specifically recognize surface receptors of particular microorganisms and thus specifically infect those microorganisms. As such, these infectious agents may be appropriate binding agents for targeting a microorganism of interest.

Some embodiments of the invention utilize the specificity of binding and high-level genetic expression capacity of recombinant bacteriophage for rapid and sensitive targeting to infect and facilitate detection of a bacterium of interest. In some embodiments, *Salmonella*-specific bacteriophage is genetically modified to include a reporter gene. In some embodiments the late gene region of a bacteriophage is genetically modified to include a reporter gene. In some embodiments, a reporter gene is positioned downstream of the major capsid gene. In other embodiments, a reporter gene is positioned upstream of the major capsid gene. In some embodiments, the inserted genetic construct further comprises its own exogenous, dedicated promoter to drive expression of the indicator gene. The exogenous promoter is in addition to any endogenous promoter in the phage genome.

As bacteriophage produce polycistronic mRNA transcripts, only a single promoter is required after the first gene/cistron in the transcript. Conventional recombinant constructs only use the endogenous bacteriophage promoter to drive inserted genes. In contrast, addition of an additional promoter upstream of the reporter gene and ribosomal binding site may increase gene expression by acting as a secondary initiation site for transcription. The complicated and compact genomes of viruses often have overlapping genes in different frames, sometimes in two different directions. Inserting an additional promoter may inadvertently interfere with these other genes, and may be a reason not to do such.

Some embodiments of methods for preparing a recombinant indicator bacteriophage include selecting a wild-type bacteriophage that specifically infects a target pathogenic bacterium, such as a *Salmonella* spp.; preparing a homologous recombination plasmid/vector that comprises an indicator gene; transforming the homologous recombination plasmid/vector into target pathogenic bacteria; infecting the transformed target pathogenic bacteria with the selected wild-type bacteriophage, thereby allowing homologous recombination to occur between the plasmid/vector and the bacteriophage genome; and isolating a particular clone of recombinant bacteriophage.

Various methods for designing and preparing a homologous recombination plasmid are known. Various methods for transforming bacteria with a plasmid are known, including heat-shock, F pilus mediated bacterial conjugation, electroporation, and other methods. Various methods for isolating a particular clone following homologous recombination are also known. Some method embodiments described herein utilize particular strategies.

Thus, some embodiments of methods for preparing indicator bacteriophage include the steps of selecting a wild-type bacteriophage that specifically infects a target pathogenic bacterium; determining the natural sequence in the late region of the genome of the selected bacteriophage; annotating the genome and identifying the major capsid protein gene of the selected bacteriophage; designing a sequence for homologous recombination adjacent to the major capsid protein gene, wherein the sequence comprises a codon-optimized reporter gene; incorporating the sequence designed for homologous recombination into a plasmid/vector; transforming the plasmid/vector into target pathogenic bacteria; selecting for the transformed bacteria; infecting the transformed bacteria with the selected wild-type bacteriophage, thereby allowing homologous recombination to occur between the plasmid and the bacteriophage genome; determining the titer of the resulting recombinant bacteriophage lysate; and performing a limiting dilution assay to enrich and isolate the recombinant bacteriophage. Some embodiments comprise further repeating the limiting dilution and titer steps, following the first limiting dilution assay, as needed until the recombinant bacteriophage represent a detectable fraction of the mixture. For example, in some embodiments the limiting dilution and titer steps can be repeated until at least 1/30 of the bacteriophage in the mixture are recombinant before isolating a particular clone of recombinant bacteriophage. A ratio of 1:30 recombinant: wild-type is expected, in some embodiments, to yield an average of 3.2 transducing units (TU) per 96 plaques (e.g., in a 96-well plate). The initial ratio of recombinant to wild-type phage may be determined by performing limiting dilution assays based on the TCID50 (tissue culture infectious dose 50%) as previously described in U.S. application Ser. No. 15/409,258. By Poisson distribution, a 1:30 ratio generates a 96% chance of observing at least one TU somewhere in the 96 wells.

FIG. 1 depicts a schematic representation of the genomic structure of a recombinant indicator bacteriophage of the invention. For the embodiment depicted in FIG. 1, the detection moiety is encoded by a luciferase gene 100 inserted within the late (class III) gene region 110, which is expressed late in the viral life cycle. Late genes are generally expressed at higher levels than other phage genes, as they code for structural proteins. Thus, in the embodiment of the recombinant phage depicted in FIG. 1, the indicator gene (i.e., luciferase) is inserted into the late gene region, just after the gene for major capsid protein (MCP) 120, and is a construct comprising the luciferase gene 100. In some embodiments, the construct depicted in FIG. 1 may include stop codons in all 3 reading frames to ensure luciferase is not incorporated into the MCP gene product via read-through of the ribosome, creating a fusion protein. Also as depicted in FIG. 1, the construct may comprise an additional, dedicated late promoter 130 to drive transcription and expression of the luciferase gene. The construct also comprises a ribosome binding site (RBS) 140. This construct ensures soluble luciferase is produced such that expression is not limited to the number of capsid proteins inherent in the phage display system.

As noted herein, in certain embodiments, it may be preferred to utilize infectious agents that have been isolated from the environment for production of the infectious agents of the invention. In this way, infectious agents that are specific to naturally derived microorganisms may be generated.

Figure 2:
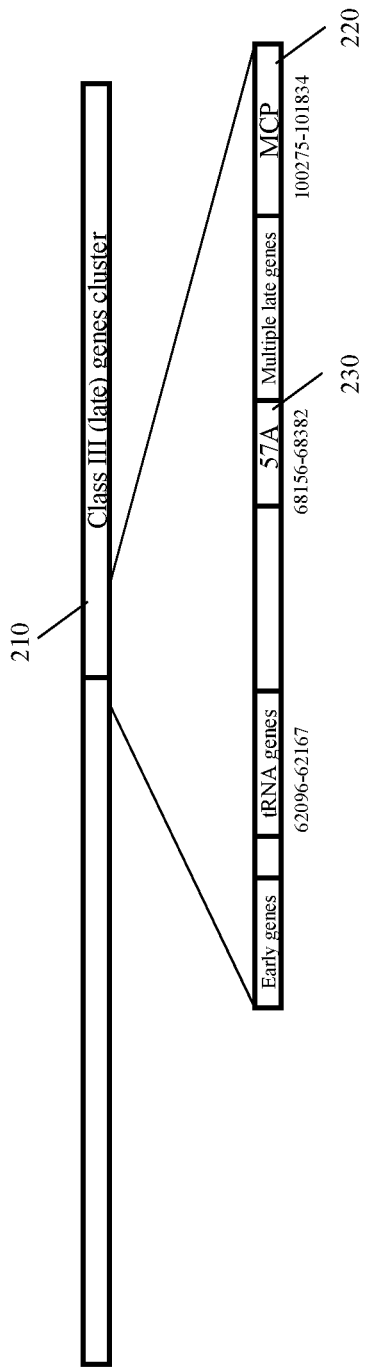
FIG. 2 shows the genome of bacteriophage SEA1, a myovirus (related to T4 bacteriophage) and shares ~95% homology with myovirus *Salmonella* Phage S16. Gene 57A chaperone for long tail fiber formation is at the periphery of the late gene region, consisting of structural genes, which code for virion proteins. As these virion proteins are expressed at a very high level, any genes inserted into this region can be expected to have similar expression levels, as long as late gene promoters and/or other similar control elements are used.

For example, FIG. 2 shows the genome of bacteriophage SEA1, a natural phage having about 95% sequence homology to a T4 related myovirus bacteriophage S16. The whole genome of the SEA1 bacteriophage was sequenced using the ILLUMINA® MISEQ™ system with de novo sequence assembly. As discussed in the Examples, the Major Capsid Protein 220 and various other structural genes are within the late gene region 210, consisting of structural genes, which code for virion proteins. Gene 57A 230, coding for chaperone for long tail fiber formation lies at the border of the late gene region. As these virion proteins are expressed at a very high level, any genes inserted into this region can be expected to have similar expression levels, as long as late gene promoters and/or other similar control elements are used.

There are numerous known methods and commercial products for preparing plasmids. For example PCR, site-directed mutagenesis, restriction digestion, ligation, cloning, and other techniques may be used in combination to prepare plasmids. Synthetic plasmids can also be ordered commercially (e.g., GeneWiz). Cosmids can also be employed, or the CRISPR/CAS9 system could be used to selectively edit a bacteriophage genome. Some embodiments of methods of preparing a recombinant indicator bacteriophage include designing a plasmid that can readily recombine with the wild-type bacteriophage genome to generate recombinant genomes. In designing a plasmid, some embodiments include addition of a codon-optimized reporter gene, such as a luciferase gene. Some embodiments further include addition of elements into the upstream untranslated region. For example, in designing a plasmid to recombine with the *Salmonella*-specific bacteriophage genome, an upstream untranslated region can be added between the sequence encoding the C-terminus of the Major Capsid Protein and the start codon of the NANOLUC® reporter gene. The untranslated region can include a promoter, such as a T4, T4-like, T7, T7-like, *Salmonella*- or *Staphylococcus*-specific bacteriophage, ViI, or ViI-like promoter. The untranslated region can also include a Ribosomal Entry/Binding Site (RBS), also known as a "Shine-Dalgarno Sequence" with bacterial systems. Either or both of these elements, or other untranslated elements, can be embedded within a short upstream untranslated region made of random sequences comprising about the same GC content as rest of the phage genome. The random region should not include an ATG sequence, as that will act as a start codon.

Figure 3:
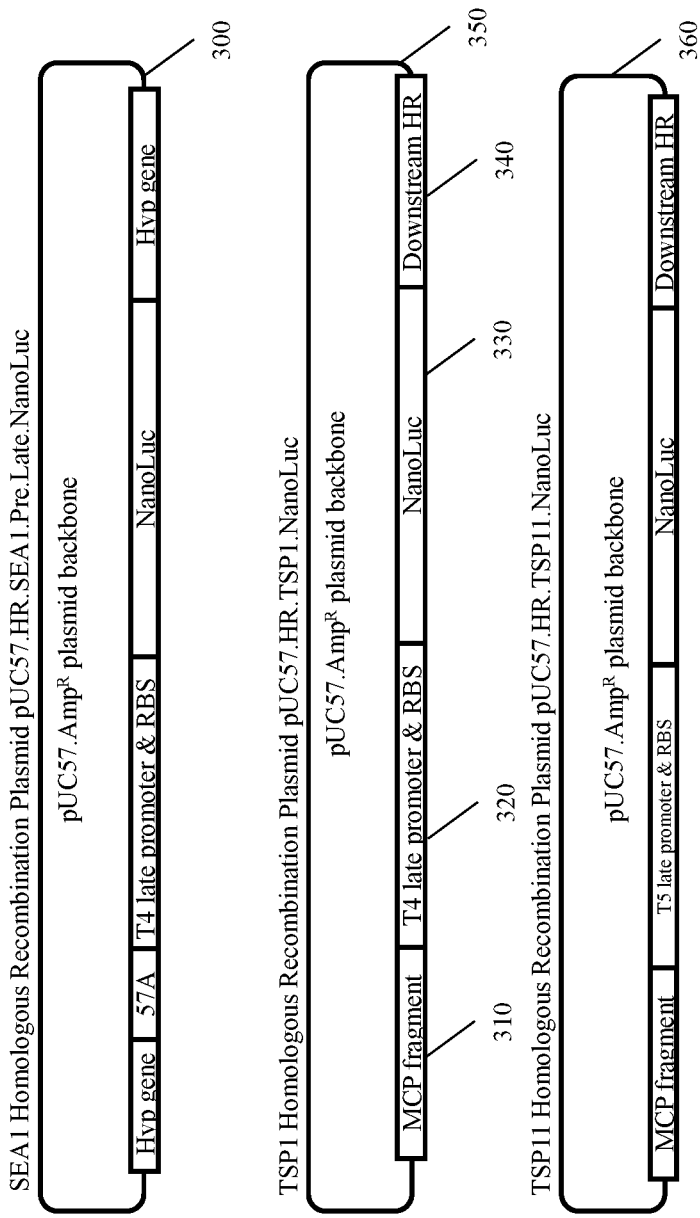
FIG. 3 shows three homologous recombination plasmid constructs carrying luciferase genes for 3 different phages with approximately 500 bp of matching phage sequence upstream and downstream of the insertion site to promote homologous recombination. NANOLUC® luciferase is inserted into a pUC57.Amp$^R$ plasmid backbone with an upstream untranslated region containing a dedicated phage late gene promoter and Ribosomal Entry/Binding Site. The *Salmonella* phage SEA1 recombination plasmid 300 was constructed to insert NANOLUC® within the late gene region, but at a distance from the Major Capsid Protein (MCP) due to stability issues. TSP1 is a newly isolated phage, related to or part of the T4likevirus genus in the myovirus family. TSP11 is a newly isolated phage, related to or part of the T5likevirus genus in the siphovirus family. Each construct consisted of 500 bp of homologous recombination sequence from the wild-type virus late gene region 310, followed by the appropriate phage late gene promoter and a ribosomal binding site 320, followed by the luciferase gene 330, and finally the downstream 500 bp homologous recombination region from the wild-type virus 340.

The compositions of the invention may comprise various infectious agents and/or indicator genes. For example, FIG. 3 shows three homologous recombination plasmid constructs used in making the indicator phage specific for *Salmonella*. Constructs were made and used in recombination with *Salmonella* phage SEA1 to generate recombinant bacteriophage of the invention. Thus, the top construct 300 in FIG. 3 shows a recombination plasmid having NANOLUC® construct used for homologous recombination insertion of the NANOLUC® luciferase into SEA1: homologous recombination plasmid pUC57.HR.SEA1.Pre.Late. NANOLUC®. Previous attempts to insert NANOLUC® adjacent to the Major Capsid Protein failed with SEA1 due to stability issues. The middle construct 350 shows a recombination plasmid having NanoLuc® construct used for homologous recombination insertion of the NanoLuc® luciferase into TSP1, a myovirus related to or within the T4likevirus genome: homologous recombination plasmid pUC57.HR.TSP1.NANOLUC®. The lower construct 360 shows a recombination plasmid having NANOLUC® construct used for homologous recombination insertion of the NANOLUC® luciferase into TSP1, a myovirus related to or within the T5likevirus genome: homologous recombination plasmid pUC57.HR.TSP11.NANOLUC®.

The Major Capsid Protein fragment is a part of a structural gene that encodes a virion protein. As these virion proteins are expressed at a very high level, any genes inserted into this region can be expected to have similar expression levels, as long as late gene promoters and/or other similar control elements are used.

In some embodiments, indicator phage according to the invention comprise Salmonella-specific bacteriophage genetically engineered to comprise a reporter gene such as a luciferase gene. For example, an indicator phage can be Salmonella-specific bacteriophage wherein the genome comprises the sequence of the NANOLUC® gene. A recombinant Salmonella-specific NanoLuc bacteriophage genome may further comprise a consensus promoter of T4, T5, T7, Salmonella-specific, ViI, bacteriophage or another late promoter. In further embodiments, the promoter is an exogenous promoter. Insertion of an exogenous promoter to drive expression of an indicator gene is advantageous in that expression is not limited by the expression of other phage proteins (e.g., the major capsid protein).

Thus, in the embodiment of the recombinant phage generated as a result of the recombination, the indicator gene (i.e., NANOLUC®) is inserted into the late gene region. In some embodiments the indicator gene is inserted downstream of the gene encoding the major capsid protein, and thus creates recombinant bacteriophage genomes comprising the NANOLUC® gene. The construct may additionally comprise the consensus promoter of T4, T5, T7, Salmonella-specific bacteriophage, ViI, or another late promoter or another suitable promoter to drive transcription and expression of the luciferase gene. The construct may also comprise a composite untranslated region synthesized from several UTRs. This construct ensures soluble luciferase is produced such that expression is not limited to the number of capsid proteins inherent in the phage display system.

Figure 4:
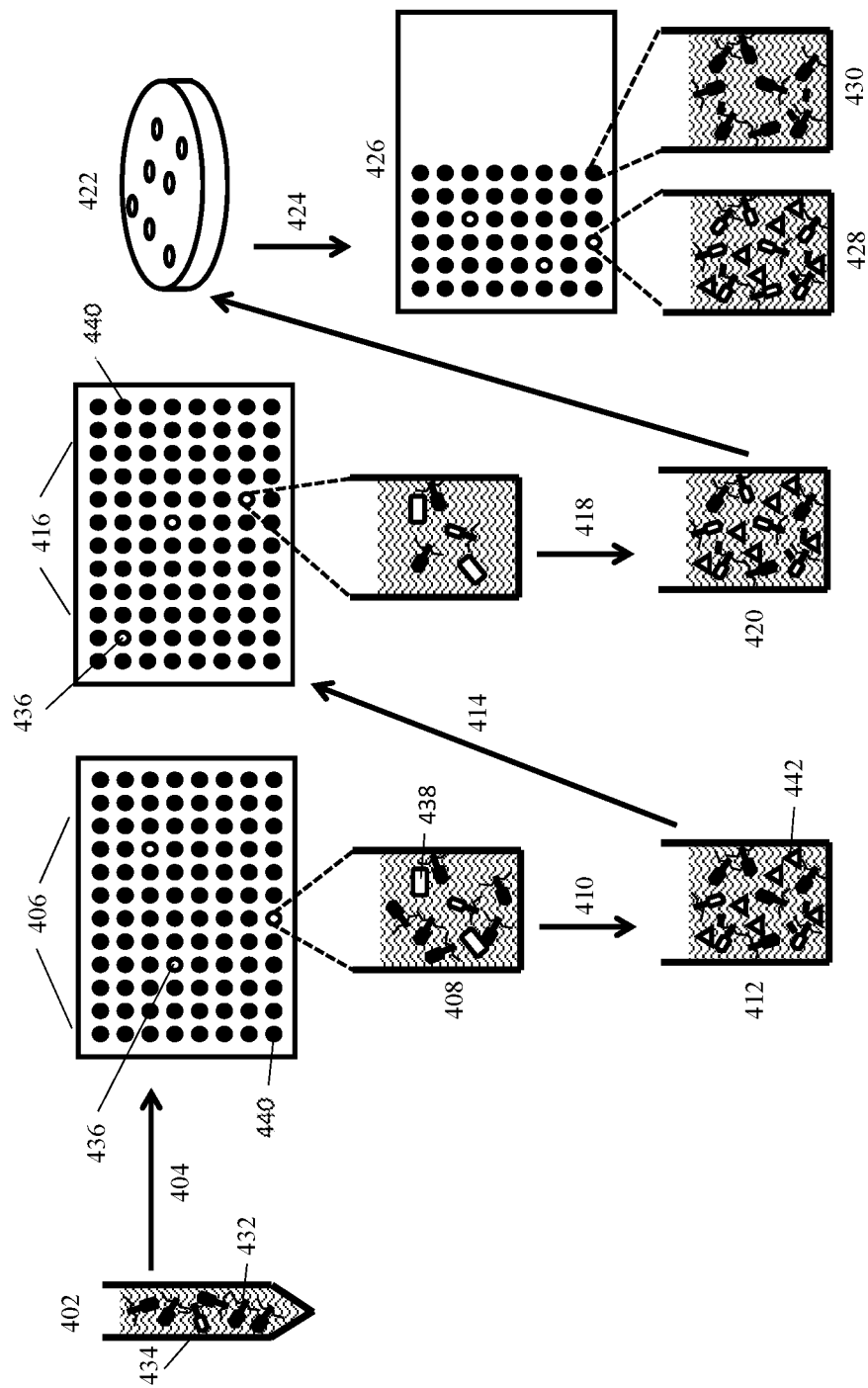
FIG. 4 depicts the isolation of recombinant phage from modifications of SEA1 bacteriophage using the plasmid constructs such as those shown in FIG. 3 using a series of sequential infection and dilution steps to identify recombinant phage that express an indicator gene.

FIG. 4 depicts the isolation of recombinant phage from the mixture of wild-type and recombinant bacteriophage resulting from the homologous recombination. In the first step 402, Salmonella spp. bacteria transformed with the homologous recombination plasmid are infected with Salmonella spp. bacteriophage SEA1, resulting in progeny phage with a mixture of parental and recombinant phage with very low ratios of wild-type to recombinant phage 434. The resulting recombinant phage mix is diluted 404 into 96-well plates 406 to give an average of 5 recombinant transducing units (TU) per plate (9.3 PFU/well). The 96-well plate is assayed for luciferase activity to identify wells 436 containing recombinant phage as compared to wells 440 containing wild-type bacteriophage. Bacteria 438 are added 408; for example, each well may contain about 50 µL of a turbid Salmonella culture. This allows the phage to replicate and produce the luciferase enzyme 442. After 5 hours of incubation at 37° C. shown in 410, wells may be screened for the presence of luciferase 442. Any positive wells are likely to have been inoculated with a single recombinant phage, and at this stage the mixture may contain a ratio of approximately 10 wild-type phage:1 recombinant, an enrichment over the original ratio. If necessary (i.e., if the ratio of recombinant:total is lower than 1:30), progeny from this enriched culture 412 may be subjected to additional limiting dilution assay(s) 414 to increase the ratio and determine the actual concentration of recombinant phage transducing units. For example, if the ratio was 1:384 recombinants:PFU, about 5 recombinant TU along with 1920 contaminating total phage (5×384=1920) per 96-well plate 416 may be aliquoted 414 from the previous positive well, leading to an approximate inoculation of 20 mostly wild-type phage per well (1920 PFU/96 wells=20 PFU/well) of a second dilution assay plate 420. Any positive luciferase wells are likely to have been inoculated with a single recombinant along with 19 wild-type phage. These wells may be analyzed for presence of luciferase 442.

After addition of bacteria and incubation (e.g., for 5 hours at 37° C.) 418, soluble luciferase and phage are present at approximately 20 total:1 recombinant 420. This ratio may be verified by TU50 titration for recombinants and plaque assay for total PFU. Finally, a plaque assay may be performed 422 to screen for recombinants that express luciferase 446. A small number of individual (e.g., n=48) plaques may be individually picked and screened in a third multiwell plate 426 for luciferase activity 436. In an embodiment, this approach should insure that enough plaques be screened so about 3 recombinants are in the mix of plaques being screened based on the known ratio of recombinants to total phage. One plaque may be removed from the plate to each well of a 96-well plate 424 and a luciferase assay performed 426 to determine which wells contained phage exhibiting luciferase activity 442. Wells 428 demonstrating luciferase activity represent pure recombinant phage 434, while wells without luciferase activity 430 represent pure wild-type phage 432.

Individual plaques may then be suspended in buffer (e.g., 100 µL TMS) or media, and an aliquot (e.g., about 5 µL) added to a well containing a turbid Salmonella spp. culture, and assayed after incubation (e.g., about 45 minutes to 1 hour at 37° C.). Positive wells are expected to contain a pure culture of recombinant phage. Certain embodiments can include additional rounds of plaque purification.

Thus, as illustrated by FIG. 4, recombinant phage generated by homologous recombination of a plasmid designed for recombination with the wild-type phage genome can be isolated from a mixture comprising a very small percentage (e.g., 0.005%) of total phage genomes. Following isolation, large scale production may be performed to obtain high titer recombinant indicator phage stocks appropriate for use in the Salmonella spp. detection assay. Furthermore, cesium chloride isopycnic density gradient centrifugation may be used to separate phage particles from contaminating luciferase protein to reduce background.

Methods of Using Infectious Agents for Detecting Microorganisms

As noted herein, in certain embodiments, the invention may comprise methods of using infectious particles for detecting microorganisms, such as Salmonella spp. The methods of the invention may be embodied in a variety of ways.

In an embodiment, the invention may comprise a method for detecting a bacterium of interest in a sample comprising the steps of: incubating the sample with bacteriophage that infects the bacterium of interest, wherein the bacteriophage comprises an indicator gene such that expression of the indicator gene during bacteriophage replication following infection of the bacterium of interest results in production of a soluble indicator protein product; and detecting the indicator protein product, wherein positive detection of the indicator protein product indicates that the bacterium of interest is present in the sample.

In certain embodiments, the assay may be performed to utilize a general concept that can be modified to accommodate different sample types or sizes and assay formats. Embodiments employing recombinant bacteriophage of the invention (i.e., indicator bacteriophage) may allow rapid detection of *Salmonella* spp., with total assay times under 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12, 12.5, 13.0, 13.5, 14.0, 14.5, 15.0, 15.5, 16.0, 16.5, 17.0, 17.5, 18.0, 18.5, 19.0, 19.5, 20.0, 21.0, 22.0, 23.0, 24.0, 25.0, or 26.0 hours, depending on the sample type, sample size, and assay format. For example, the amount of time required may be somewhat shorter or longer depending on the strain of bacteriophage and the strain of bacteria to be detected in the assay, type and size of the sample to be tested, conditions required for viability of the target, complexity of the physical/chemical environment, and the concentration of "endogenous" non-target bacterial contaminants.

Figure 5:
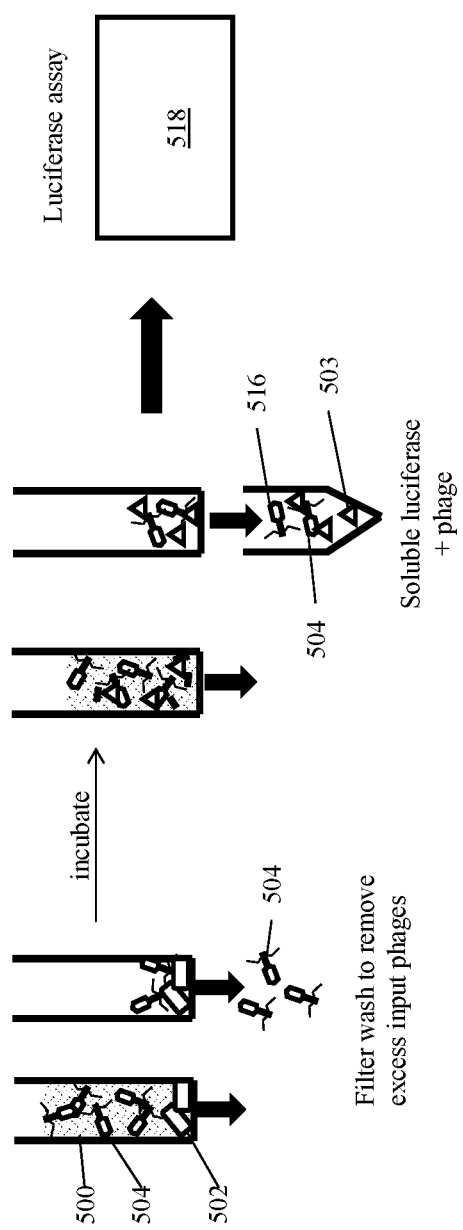
FIG. 5 depicts the use of indicator phage encoding a soluble luciferase to detect bacterial cells via detection of luciferase generated from replication of progeny phage during infection of the bacterial cells, according to an embodiment of the invention.

FIG. 5 shows a strategy of using indicator phage that produce soluble luciferase according to an embodiment of the invention. In this method, the phage (e.g., TSP1, TSP11, SEA1 phage) may be engineered to express a soluble luciferase during replication of the phage. Expression of luciferase is driven by a viral capsid promoter (e.g., the bacteriophage T5 or T4 late promoter), yielding high expression. Parental phage will be free of luciferase, so the luciferase detected in the assay must come from replication of progeny phage during infection of the bacterial cells. Thus, there is generally no need to separate out the parental phage from the progeny phage.

In these experiments, at least part of the sample 500 comprising the bacteria 502 to be quantified is placed in a spin column filter and centrifuged to remove the LB broth, and an appropriate multiplicity of phage 504 genetically engineered to express soluble luciferase 503 are added. The infected cells may be incubated for a time sufficient for replication of progeny phage and cell lysis to occur (e.g., 30-120 minutes at 37° C.). The parental 504 and progeny phage 516 plus free luciferase 503 in the lysate may then be collected, e.g., by centrifugation, and the level of luciferase in the filtrate quantified using a luminometer 518. Alternatively, a high through-put method may be employed where bacterial samples are applied to a 96-well filter plate, and after all manipulations listed above are performed, may be directly assayed for luciferase in the original 96-well filter plate without a final centrifugation step.

Figure 6:
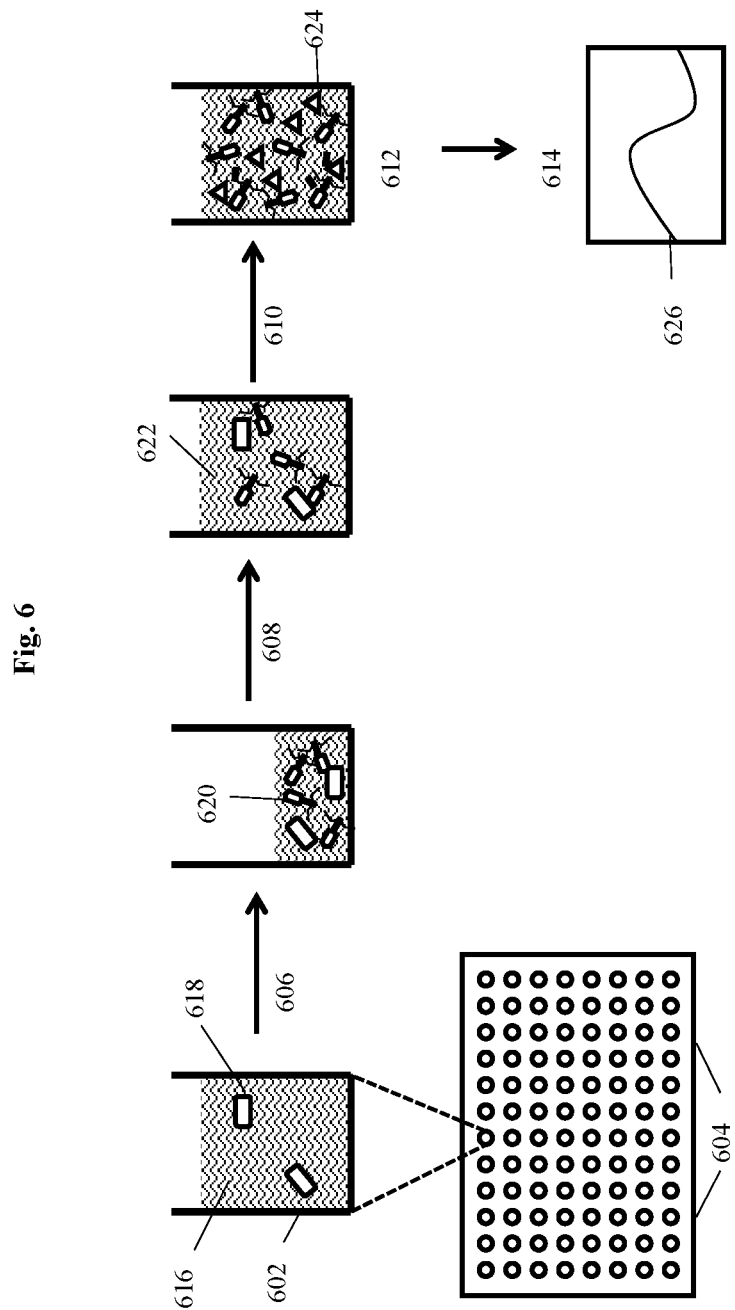
FIG. 6 depicts a filter plate assay for detecting bacteria of interest using a modified bacteriophage according to an embodiment of the invention where bacteria and recombinant phage are incubated on filter plates and after generation of progeny bacteriophage the indicator protein is detected directly without removal of the incubation medium.

FIG. 6 depicts a filter plate assay for detecting bacteria of interest using a modified bacteriophage according to an embodiment of the invention. Briefly, samples 616 that include a bacterium of interest 618 may be added to wells 602 of a multi-well filter plate 604 and spun 606 to concentrate the samples by removal of liquid from the sample. Genetically modified phage 620 are added to wells and incubated with additional media added for enough time sufficient for adsorption 608 followed by infection of target bacteria and advancement of the phage life cycle 610 (e.g., ~45 minutes). Finally, luciferase substrate is added and reacts with any luciferase present 624. The resulting emission is measured in a luminometer 614 which detects luciferase activity 626.

Figure 7:
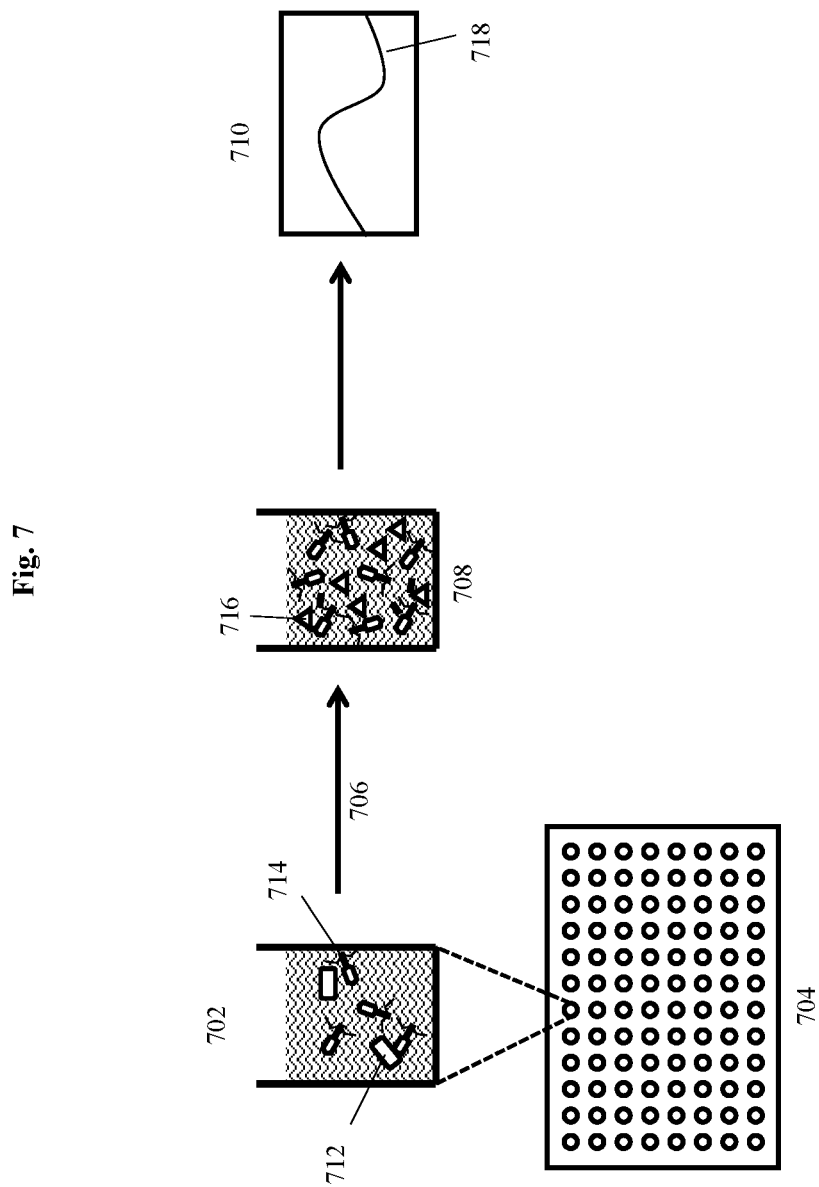
FIG. 7 depicts a "No Concentration Assay" for detecting a bacterium of interest using a modified bacteriophage according to an embodiment of the invention.

In certain embodiments, the assay may be performed without concentrating the bacterium on or near the capture surface. FIG. 7 illustrates a "No Concentration Assay" for detecting a bacterium of interest using a modified bacteriophage according to an embodiment of the invention. Aliquots of indicator phage 714 are distributed to the individual wells 702 of a multi-well plate 704, and then test sample aliquots containing bacteria 712 are added and incubated 706 (e.g., 45 minutes at 37° C.) for a period of time sufficient for phage to replicate and generate soluble indicator 716 (e.g., luciferase). The plate wells 708 containing soluble indicator and phage may then be assayed 710 to measure the indicator activity on the plate 718 (e.g., luciferase assay). In this embodiment, the test samples are not concentrated (e.g., by centrifugation) but are simply incubated directly with indicator phage for a period of time and subsequently assayed for luciferase activity.

In some embodiments, the sample may be enriched prior to testing by incubation in conditions that encourage growth. In such embodiments, the enrichment period can be 1, 2, 3, 4, 5, 6, 7, 8, 9, 10, 11, 12, 13, 14, 15, 16, 17, 18, 19, 20, 21, 22, 23, 24, hours or longer, depending on the sample type and size.

In some embodiments, the indicator bacteriophage comprises a detectable indicator moiety, and infection of a single pathogenic cell (e.g., bacterium) can be detected by an amplified signal generated via the indicator moiety. Thus the method may comprise detecting an indicator moiety produced during phage replication, wherein detection of the indicator indicates that the bacterium of interest is present in the sample.

In an embodiment, the invention may comprise a method for detecting a bacterium of interest in a sample comprising the steps of: incubating the sample with a recombinant bacteriophage that infects the bacterium of interest, wherein the recombinant bacteriophage comprises an indicator gene inserted into a late gene region of the bacteriophage such that expression of the indicator gene during bacteriophage replication following infection of host bacteria results in production of a soluble indicator protein product; and detecting the indicator protein product, wherein positive detection of the indicator protein product indicates that the bacterium of interest is present in the sample. In some embodiments, the amount of indicator moiety detected corresponds to the amount of the bacterium of interest present in the sample.

As described in more detail herein, the methods and systems of the invention may utilize a range of concentrations of parental indicator bacteriophage to infect bacteria present in the sample. In some embodiments the indicator bacteriophage are added to the sample at a concentration sufficient to rapidly find, bind, and infect target bacteria that are present in very low numbers in the sample, such as a single cell. In some embodiments, the phage concentration can be sufficient to find, bind, and infect the target bacteria in less than one hour. In other embodiments, these events can occur in less than two hours, or less than three hours, following addition of indicator phage to the sample. For example, in certain embodiments, the bacteriophage concentration for the incubating step is greater than $1 \times 10^5$ PFU/mL, greater than $1 \times 10^6$ PFU/mL, or greater than $1 \times 10^7$ PFU/mL.

In certain embodiments, the recombinant infectious agent may be purified so as to be free of any residual indicator protein that may be generated upon production of the infectious agent stock. Thus, in certain embodiments, the recombinant bacteriophage may be purified using cesium chloride isopycnic density gradient centrifugation prior to incubation with the sample. When the infectious agent is a bacteriophage, this purification may have the added benefit of removing bacteriophage that do not have DNA (i.e., empty phage or "ghosts").

In some embodiments of the methods of the invention, the microorganism may be detected without any isolation or purification of the microorganisms from a sample. For example, in certain embodiments, a sample containing one or a few microorganisms of interest may be applied directly to an assay container such as a spin column, a microtiter well, or a filter and the assay is conducted in that assay container. Various embodiments of such assays are disclosed herein.

Aliquots of a test sample may be distributed directly into wells of a multi-well plate, indicator phage may be added, and after a period of time sufficient for infection, a lysis buffer may be added as well as a substrate for the indicator moiety (e.g., luciferase substrate for a luciferase indicator) and assayed for detection of the indicator signal. Some embodiments of the method can be performed on filter plates. Some embodiments of the method can be performed with or without concentration of the sample before infection with indicator phage.

For example, in many embodiments, multi-well plates are used to conduct the assays. The choice of plates (or any other container in which detecting may be performed) may affect the detecting step. For example, some plates may include a colored or white background, which may affect the detection of light emissions. Generally speaking, white plates have higher sensitivity but also yield a higher background signal. Other colors of plates may generate lower background signal but also have a slightly lower sensitivity. Additionally, one reason for background signal is the leakage of light from one well to another, adjacent well. There are some plates that have white wells but the rest of the plate is black. This allows for a high signal inside the well but prevents well-to-well light leakage and thus may decrease background. Thus the choice of plate or other assay vessel may influence the sensitivity and background signal for the assay.

Methods of the invention may comprise various other steps to increase sensitivity. For example, as discussed in more detail herein, the method may comprise a step for washing the captured and infected bacterium, after adding the bacteriophage but before incubating, to remove excess parental bacteriophage and/or luciferase or other reporter protein contaminating the bacteriophage preparation.

In some embodiments, detection of the microorganism of interest may be completed without the need for culturing the sample as a way to increase the population of the microorganisms. For example, in certain embodiments the total time required for detection is less than 26.0 hours, 25.0 hours, 24.0 hours, 23.0 hours, 22.0 hours, 21.0 hours, 20.0 hours, 19.0 hours, 18.0 hours, 17.0 hours, 16.0 hours, 15.0 hours, 14.0 hours, 13.0 hours, 12.0 hours, 11.0 hours, 10.0 hours, 9.0 hours, 8.0 hours, 7.0 hours, 6.0 hours, 5.0 hours, 4.0 hours, 3.0 hours, 2.5 hours, 2.0 hours, 1.5 hours, 1.0 hour, 45 minutes, or less than 30 minutes. Minimizing time to result is critical in food and environmental testing for pathogens.

In contrast to assays known in the art, the method of the invention can detect individual microorganisms. Thus, in certain embodiments, the method may detect ≤10 cells of the microorganism (i.e., 1, 2, 3, 4, 5, 6, 7, 8, 9 microorganisms) present in a sample. For example, in certain embodiments, the recombinant bacteriophage is highly specific for *Salmonella* spp. In an embodiment, the recombinant bacteriophage can distinguish *Salmonella* spp. in the presence of other types of bacteria. In certain embodiments, the recombinant bacteriophage can be used to detect a single bacterium of the specific type in the sample. In certain embodiments, the recombinant bacteriophage detects as few as 2, 3, 4, 5, 6, 7, 8, 9, 10, 15, 20, 30, 40, 50, 60, 70, 80, 90, or 100 of the specific bacteria in the sample.

Thus, aspects of the present invention provide methods for detection of microorganisms in a test sample via an indicator moiety. In some embodiments, where the microorganism of interest is a bacterium, the indicator moiety may be associated with an infectious agent such as an indicator bacteriophage. The indicator moiety may react with a substrate to emit a detectable signal or may emit an intrinsic signal (e.g., fluorescent protein). In some embodiments, the detection sensitivity can reveal the presence of as few as 50, 20, 10, 9, 8, 7, 6, 5, 4, 3, or 2 cells of the microorganism of interest in a test sample. In some embodiments, even a single cell of the microorganism of interest may yield a detectable signal. In some embodiments, the bacteriophage is a T4-like or ViI-like bacteriophage. In some embodiments, the recombinant bacteriophage is derived from *Salmonella*-specific bacteriophage. In certain embodiments, a recombinant *Salmonella*-specific bacteriophage is highly specific for *Salmonella* spp.

In some embodiments, the indicator moiety encoded by the infectious agent may be detectable during or after replication of the infectious agent. Many different types of detectable biomolecules suitable for use as indicator moieties are known in the art, and many are commercially available. In some embodiments the indicator phage comprises an enzyme, which serves as the indicator moiety. In some embodiments, the genome of the indicator phage is modified to encode a soluble protein. In some embodiments, the indicator phage encodes a detectable enzyme. The indicator may emit light and/or may be detectable by a color change. Various appropriate enzymes are commercially available, such as alkaline phosphatase (AP), horseradish peroxidase (HRP), or luciferase (Luc). In some embodiments, these enzymes may serve as the indicator moiety. In some embodiments, Firefly luciferase is the indicator moiety. In some embodiments, Oplophorus luciferase is the indicator moiety. In some embodiments, NANOLUC® is the indicator moiety. Other engineered luciferases or other enzymes that generate detectable signals may also be appropriate indicator moieties.

Thus, in some embodiments, the recombinant bacteriophage of the methods, systems or kits is prepared from wild-type *Salmonella*-specific bacteriophage. In some embodiments, the indicator gene encodes a protein that emits an intrinsic signal, such as a fluorescent protein (e.g., green fluorescent protein or others). The indicator may emit light and/or may be detectable by a color change. In some embodiments, the indicator gene encodes an enzyme (e.g., luciferase) that interacts with a substrate to generate signal. In some embodiments, the indicator gene is a luciferase gene. In some embodiments, the luciferase gene is one of Oplophorus luciferase, Firefly luciferase, Renilla luciferase, External Gaussia luciferase, Lucia luciferase, or an engineered luciferase such as NANOLUC®, Rluc8.6-535, or Orange Nano-lantern.

Detecting the indicator may include detecting emissions of light. In some embodiments, a luminometer may be used to detect the reaction of indicator (e.g., luciferase) with a substrate. The detection of RLU can be achieved with a luminometer, or other machines or devices may also be used. For example, a spectrophotometer, CCD camera, or CMOS camera may detect color changes and other light emissions. Absolute RLU are important for detection, but the signal to background ratio also needs to be high (e.g., >2.0, >2.5, or >3.0) in order for single cells or low numbers of cells to be detected reliably.

In some embodiments, the indicator phage is genetically engineered to contain the gene for an enzyme, such as a luciferase, which is only produced upon infection of bacteria that the phage specifically recognizes and infects. In some embodiments, the indicator moiety is expressed late in the viral life cycle. In some embodiments, as described herein, the indicator is a soluble protein (e.g., soluble luciferase) and is not fused with a phage structural protein that limits its copy number.

Thus in some embodiments utilizing indicator phage, the invention comprises a method for detecting a microorganism of interest comprising the steps of capturing at least one sample bacterium; incubating the at least one bacterium with a plurality of indicator phage; allowing time for infection and replication to generate progeny phage and express soluble indicator moiety; and detecting the progeny phage, or preferably the indicator, wherein detection of the indicator demonstrates that the bacterium is present in the sample.

For example, in some embodiments the test sample bacterium may be captured by binding to the surface of a plate, or by filtering the sample through a bacteriological filter (e.g., 0.45 µm pore size spin filter or plate filter). In an embodiment, the infectious agent (e.g., indicator phage) is added in a minimal volume to the captured sample directly on the filter. In an embodiment, the microorganism captured on the filter or plate surface is subsequently washed one or more times to remove excess unbound infectious agent. In an embodiment, a medium (e.g., Luria-Bertani Broth, also called LB herein, or Tryptic Soy Broth or Tryptone Soy Broth, also called TSB herein, or Buffered Peptone Water, also called BPW herein) may be added for further incubation time, to allow replication of bacterial cells and phage and high-level expression of the gene encoding the indicator moiety. However, a surprising aspect of some embodiments of testing assays is that the incubation step with indicator phage only needs to be long enough for a single phage life cycle. The amplification power of using bacteriophage was previously thought to require more time, such that the phage would replicate for several cycles. A single replication cycle of indicator phage can be sufficient to facilitate sensitive and rapid detection according to some embodiments of the present invention.

In some embodiments, aliquots of a test sample comprising bacteria may be applied to a spin column and after infection with a recombinant bacteriophage and an optional washing to remove any excess bacteriophage, the amount of soluble indicator detected will be proportional to the amount of bacteriophage that are produced by infected bacteria.

Soluble indicator (e.g., luciferase) released into the surrounding liquid upon lysis of the bacteria may then be measured and quantified. In an embodiment, the solution is spun through the filter, and the filtrate collected for assay in a new receptacle (e.g., in a luminometer) following addition of a substrate for the indicator enzyme (e.g., luciferase substrate). Alternatively, the indicator signal may be measured directly on the filter.

In various embodiments, the purified parental indicator phage does not comprise the detectable indicator itself, because the parental phage can be purified before it is used for incubation with a test sample. Expression of late (Class III) genes occurs late in the viral life cycle. In some embodiments of the present invention, parental phage may be purified to exclude any existing indicator protein (e.g., luciferase). In some embodiments, expression of the indicator gene during bacteriophage replication following infection of host bacteria results in a soluble indicator protein product. Thus, in many embodiments, it is not necessary to separate parental from progeny phage prior to the detecting step. In an embodiment, the microorganism is a bacterium and the indicator phage is a bacteriophage. In an embodiment, the indicator moiety is soluble luciferase, which is released upon lysis of the host microorganism.

Thus, in an alternate embodiment, the indicator substrate (e.g., luciferase substrate) may be incubated with the portion of the sample that remains on a filter or bound to a plate surface. Accordingly, in some embodiments the solid support is a 96-well filter plate (or regular 96-well plate), and the substrate reaction may be detected by placing the plate directly in the luminometer.

For example, in an embodiment, the invention may comprise a method for detecting Salmonella spp. comprising the steps of: infecting cells captured on a 96-well filter plate with a plurality of parental indicator phage capable of expressing luciferase upon infection; washing excess phage away; adding TSB broth and allowing time for phage to replicate and lyse the specific Salmonella spp. target (e.g., 30-120 minutes); and detecting the indicator luciferase by adding luciferase substrate and measuring luciferase activity directly in the 96-well plate, wherein detection of luciferase activity indicates that the Salmonella spp. is present in the sample.

In another embodiment, the invention may comprise a method for detecting Salmonella spp. comprising the steps of: infecting cells in liquid solution or suspension in a 96-well plate with a plurality of parental indicator phage capable of expressing luciferase upon infection; allowing time for phage to replicate and lyse the specific Salmonella spp. target (e.g., 30-120 minutes); and detecting the indicator luciferase by adding luciferase substrate and measuring luciferase activity directly in the 96-well plate, wherein detection of luciferase activity indicates that the Salmonella spp. is present in the sample. In such an embodiment no capturing step is necessary. In some embodiments, the liquid solution or suspension may be a consumable test sample, such as a vegetable wash. In some embodiments, the liquid solution or suspension may be vegetable wash fortified with concentrated LB Broth, Tryptic/Tryptone Soy Broth, Buffered Peptone Water or Nutrient Broth. In some embodiments, the liquid solution or suspension may be bacteria diluted in TSB Broth.

In some embodiments, lysis of the bacterium may occur before, during, or after the detection step. Experiments suggest that infected unlysed cells may be detectable upon addition of luciferase substrate in some embodiments. Presumably, luciferase may exit cells and/or luciferase substrate may enter cells without complete cell lysis. Thus, for embodiments utilizing the spin filter system, where only luciferase released into the lysate (and not luciferase still inside intact bacteria) is analyzed in the luminometer, lysis is required for detection. However, for embodiments utilizing filter plates or 96-well plates with sample in solution or suspension, where the original plate full of intact and lysed cells is directly assayed in the luminometer, lysis is not necessary for detection.

In some embodiments, the reaction of indicator moiety (e.g., luciferase) with substrate may continue for 30 minutes or more, and detection at various time points may be desirable for optimizing sensitivity. For example, in embodiments using 96-well filter plates as the solid support and luciferase as the indicator, luminometer readings may be taken initially and at 10- or 15-minute intervals until the reaction is completed.

Surprisingly, high concentrations of phage utilized for infecting test samples have successfully achieved detection of very low numbers of target microorganism in a very short timeframe. The incubation of phage with a test sample in some embodiments need only be long enough for a single phage life cycle. In some embodiments, the bacteriophage concentration for this incubating step is greater than $7\times10^6$, $8\times10^6$, $9\times10^6$, $1.0\times10^7$, $1.1\times10^7$, $1.2\times10^7$, $1.3\times10^7$, $1.4\times10^7$, $1.5\times10^7$, $1.6\times10^7$, $1.7\times10^7$, $1.8\times10^7$, $1.9\times10^7$, $2.0\times10^7$, $3.0\times10^7$, $4.0\times10^7$, $5.0\times10^7$, $6.0\times10^7$, $7.0\times10^7$, $8.0\times10^7$, $9.0\times10^7$, or $1.0\times10^8$ PFU/mL.

Success with such high concentrations of phage is surprising because the large numbers of phage were previously associated with "lysis from without," which killed target cells and thereby prevented generation of useful signal from earlier phage assays. It is possible that the clean-up of prepared phage stocks described herein helps to alleviate this problem (e.g., clean-up by cesium chloride isopycnic density gradient ultracentrifugation), because in addition to removing any contaminating luciferase associated with the phage, this clean-up may also remove ghost particles (particles that have lost DNA). The ghost particles can lyse bacterial cells via "lysis from without," killing the cells prematurely and thereby preventing generation of indicator signal. Electron microscopy demonstrates that a crude phage lysate (i.e., before cesium chloride clean-up) may have greater than 50% ghosts. These ghost particles may contribute to premature death of the microorganism through the action of many phage particles puncturing the cell membrane. Thus ghost particles may have contributed to previous problems where high PFU concentrations were reported to be detrimental. Moreover, a very clean phage prep allows the assay to be performed with no wash steps, which makes the assay possible to perform without an initial concentration step. Some embodiments do include an initial concentration step, and in some embodiments this concentration step allows a shorter enrichment incubation time.

Some embodiments of testing methods may further include confirmatory assays. A variety of assays are known in the art for confirming an initial result, usually at a later point in time. For example, the samples can be cultured (e.g., CHROMAGAR®/DYNABEADS® assay as described in the EXAMPLES), PCR can be utilized to confirm the presence of the microbial DNA, or other confirmatory assays can be used to confirm the initial result.

In certain embodiments, the methods of the present invention combine the use of a binding agent (e.g., antibody) to purify and/or concentrate a microorganism of interest, such as *Salmonella* spp., from the sample in addition to detection with an infectious agent. For example, in certain embodiments, the present invention comprises a method for detecting a microorganism of interest in a sample comprising the steps of: capturing the microorganism, such as *Salmonella* spp., from the sample on a prior support using a capture antibody specific to the microorganism of interest, such as *Salmonella* spp.; incubating the sample with a recombinant bacteriophage that infects the microorganism of interest, such as *Salmonella* spp., wherein the recombinant bacteriophage comprises an indicator gene inserted into a late gene region of the bacteriophage such that expression of the indicator gene during bacteriophage replication following infection of host bacteria results in a soluble indicator protein product; and detecting the indicator protein product, wherein positive detection of the indicator protein product indicates that the microorganism of interest is present in the sample.

Figure 8:
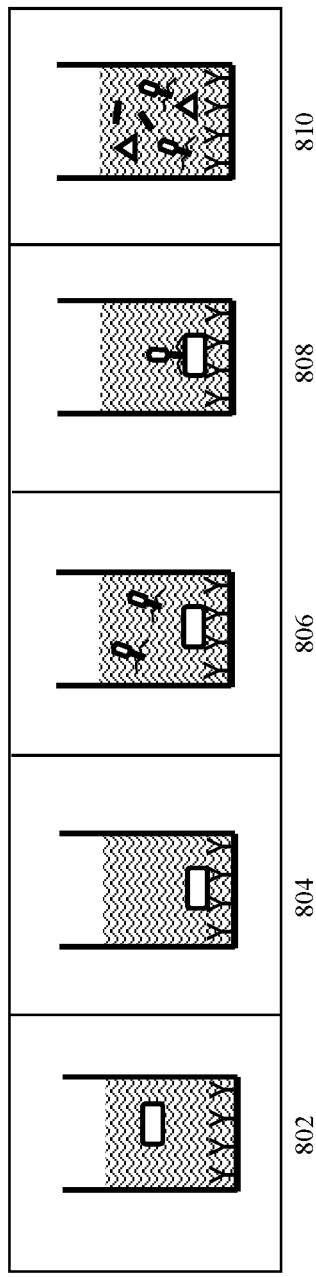
FIG. 8 depicts a Hybrid Immuno-Phage (HIP) Assay for detecting a bacterium of interest using a modified bacteriophage according to an embodiment of the invention wherein antibodies to the microorganism of interest are used to capture the microorganism on the surface of the assay well prior to incubation with a recombinant infectious agent having an indicator gene.

For example, FIG. 8 depicts a Hybrid Immuno-Phage (HIP) Assay for detecting a bacterium of interest using a modified bacteriophage according to an embodiment of the invention. The sample is first applied to the microtiter plate well coated with bacterium-specific antibodies 802. The plate is then centrifuged to facilitate binding of the bacterium to the capture antibodies 804. Following sufficient time to allow for complete bacteria capture, a solution containing bacterium-specific NANOLUC®-phage is added to each sample 806. Incubation with the phage results in the binding and attachment of a single or multiple phages to the captured bacterium 808. Finally, the sample is incubated to facilitate phage replication and luciferase expression, which leads to cell lysis and release of soluble luciferase 810.

In some embodiments, indicator phage can be employed to test initial patient samples for the presence of particular pathogens, such as a particular genus or species of bacterium. In some embodiments, the indicator phage may be used to detect a particular pathogen in a clinical sample. In this way the indicator phage can be used as a companion diagnostic, so as to evaluate the potential efficacy for specific therapeutic phages in the context of a given patient's infection or other pathogenic medical condition. In some embodiments the companion diagnostic indicator phage can be prepared by genetic modification of naturally occurring bacteriophages as previously described.

In some embodiments, the indicator phage prepared through synthetic technologies may be used for non-clinical uses. For example, the indicator phage may be used as a food safety diagnostic to identify the presence of a particular bacteria in food. In other embodiments, the companion diagnostic indicator phage can be prepared through synthetic technologies. For example, a synthetic phage genome can be designed and constructed for transformation and propagation of corresponding phage in various types of bacteria. In some instances, the synthetic biology techniques can be used to generate an indicator phage using the indicator phage target bacteria. In other instances a more convenient bacteria can be used generate an indicator phage.

In some embodiments synthetic phage are designed to optimize desirable traits for use in pathogen detection assays. In some embodiments bioinformatics and previous analyses of genetic modifications are employed to optimize desirable traits. For example, in some embodiments, the genes encoding phage tail proteins can be optimized to recognize and bind to particular species of bacteria. In other embodiments the genes encoding phage tail proteins can be optimized to recognize and bind to an entire genus of bacteria, or a particular group of species within a genus. In this way, the phage can be optimized to detect broader or narrower groups of pathogens. In some embodiments, the synthetic phage may be designed to improve expression of the reporter gene. Additionally and/or alternatively, in some instances, the synthetic phage may be designed to increase the burst size of the phage to improve detection.

In some embodiments, the stability of the phage may be optimized to improve shelf-life. For example, enzybiotic solubility may be increased in order to increase subsequent phage stability. Additionally and/or alternatively phage thermostability may be optimized. Thermostable phage better preserve functional activity during storage thereby increasing shelf-life. Thus, in some embodiments, the thermostability and/or pH tolerance may be optimized.

Some species of bacteria build biofilms to protect themselves against attacks by the immune system. These biofilms can make it difficult to effectively target bacteria. A number of enzymes (e.g., glycoside hydrolases PelAh and PslGh) have been identified that are capable of breaking down bacterial biofilm. In some embodiments, phage can be modified to code for either soluble or fusion virion proteins to allow incorporation of enzymes to break down biofilms.

In some embodiments the genetically modified phage or the synthetically derived phage comprises a detectable indicator. In some embodiments the indicator is a luciferase. In some embodiments the phage genome comprises an indicator gene (e.g., a luciferase gene or another gene encoding a detectable indicator).

In some embodiments the indicator phage, whether synthetically prepared or not, can be used to detect pathogens in patient samples subsequent to the initiation of some type of treatment. In other embodiments, the treatment can be an antibiotic (e.g., a traditional antibiotic such as penicillin or cyclosporine). In other embodiments, the treatment can be another type of drug or therapy. In this way the indicator phage can be used to monitor the progress or efficacy of any type of treatment or therapy. In some embodiments indicator phage can be used to detect and monitor the pathogenic content of patient samples taken hours or days after the initiation of treatment.

Systems and Kits of the Invention

In some embodiments, the invention comprises systems (e.g., automated systems or kits) comprising components for performing the methods disclosed herein. In some embodiments, indicator phage are comprised in systems or kits according to the invention. Methods described herein may also utilize such indicator phage systems or kits. Some embodiments described herein are particularly suitable for automation and/or kits, given the minimal amount of reagents and materials required to perform the methods. In certain embodiments, each of the components of a kit may comprise a self-contained unit that is deliverable from a first site to a second site.

In some embodiments, the invention comprises systems or kits for rapid detection of a microorganism of interest in a sample. The systems or kits may in certain embodiments comprise a component for incubating the sample with an infectious agent specific for the microorganism of interest, wherein the infectious agent comprises an indicator moiety and a component for detecting the indicator moiety. In some embodiments of both the systems and the kits of the invention, the infectious agent is a recombinant bacteriophage that infects the bacterium of interest, and the recombinant bacteriophage comprises an indicator gene inserted into a late gene region of the bacteriophage as the indicator moiety such that expression of the indicator gene during bacteriophage replication following infection of host bacteria results in a soluble indicator protein product. Some systems further comprise a component for capturing the microorganism of interest on a solid support.

In other embodiments, the invention comprises a method, system, or kit for rapid detection of a microorganism of interest in a sample, comprising an infectious agent component that is specific for the microorganism of interest, wherein the infectious agent comprises an indicator moiety, and a component for detecting the indicator moiety. In some embodiments, the bacteriophage is a T4-like, T5-like, ViI, ViI-like, or *Salmonella*-specific bacteriophage. In one embodiment, the recombinant bacteriophage is derived from *Salmonella*-specific bacteriophage. In certain embodiments, the recombinant bacteriophage is highly specific for a particular bacterium. For example, in certain embodiments, the recombinant bacteriophage is highly specific for *Salmonella* spp. In one embodiment, the recombinant bacteriophage can distinguish *Salmonella* spp. in the presence of other types of bacteria. In certain embodiments, a system or kit detects as few as 2, 3, 4, 5, 6, 7, 8, 9, 10, 15, 20, 30, 40, 50, 60, 70, 80, 90, or 100 specific bacteria in the sample.

In certain embodiments, the systems and/or kits may further comprise a component for washing the captured microorganism sample. Additionally or alternatively, the systems and/or kits may further comprise a component for determining amount of the indicator moiety, wherein the amount of indicator moiety detected corresponds to the amount of microorganism in the sample. For example, in certain embodiments, the system or kit may comprise a luminometer or other device for measuring a luciferase enzyme activity.

In some systems and/or kits, the same component may be used for multiple steps. In some systems and/or kits, the steps are automated or controlled by the user via computer input and/or wherein a liquid-handling robot performs at least one step.

Thus in certain embodiments, the invention may comprise a system or kit for rapid detection of a microorganism of interest in a sample, comprising: a component for incubating the sample with an infectious agent specific for the microorganism of interest, wherein the infectious agent comprises an indicator moiety; a component for capturing the microorganism from the sample on a solid support; a component for washing the captured microorganism sample to remove unbound infectious agent; and a component for detecting the indicator moiety. In some embodiments, the same component may be used for steps of capturing and/or incubating and/or washing (e.g., a filter component). Some embodiments additionally comprise a component for determining amount of the microorganism of interest in the sample, wherein the amount of indicator moiety detected corresponds to the amount of microorganism in the sample. Such systems can include various embodiments and subembodiments analogous to those described above for methods of rapid detection of microorganisms. In an embodiment, the microorganism is a bacterium and the infectious agent is a bacteriophage. In a computerized system, the system may be fully automated, semi-automated, or directed by the user through a computer (or some combination thereof).

In some embodiments, the system may comprise a component for isolating the microorganism of interest from the other components in the sample.

In an embodiment, the invention comprises a system or kit comprising components for detecting a microorganism of interest comprising: a component for isolating at least one microorganism from other components in the sample; a component for infecting the at least one microorganism with a plurality of a parental infectious agent; a component for lysing the at least one infected microorganism to release progeny infectious agents present in the microorganism; and a component for detecting the progeny infectious agents, or with greater sensitivity, a soluble protein encoded and expressed by the infectious agent, wherein detection of the infectious agent or a soluble protein product of the infectious agent indicates that the microorganism is present in the sample. The infectious agent may comprise *Salmonella*-specific NANOLUC™ bacteriophage.

The systems or kits may comprise a variety of components for detection of progeny infectious agents. For example, in an embodiment, the progeny infectious agent (e.g., bacteriophage) may comprise an indicator moiety. In an embodiment, the indicator moiety in the progeny infectious agent (e.g., bacteriophage) may be a detectable moiety that is expressed during replication, such as a soluble luciferase protein.

In other embodiments, the invention may comprise a kit for rapid detection of a microorganism of interest in a sample, the system comprising: a component for incubating the sample with an infectious agent specific for the microorganism of interest, wherein the infectious agent comprises an indicator moiety; a component for capturing the microorganism from the sample on a solid support; a component for washing the captured microorganism sample to remove unbound infectious agent; and a component for detecting the indicator moiety. In some embodiments, the same component may be used for steps of capturing and/or incubating and/or washing. Some embodiments additionally comprise a component for determining amount of the microorganism of interest in the sample, wherein the amount of indicator moiety detected corresponds to the amount of microorganism in the sample. Such kits can include various embodiments and subembodiments analogous to those described above for methods of rapid detection of microorganisms. In an embodiment, the microorganism is a bacterium and the infectious agent is a bacteriophage.

In some embodiments, a kit may comprise a component for isolating the microorganism of interest from the other components in the sample.

These systems and kits of the invention include various components. As used herein, the term "component" is broadly defined and includes any suitable apparatus or collections of apparatuses suitable for carrying out the recited method. The components need not be integrally connected or situated with respect to each other in any particular way. The invention includes any suitable arrangements of the components with respect to each other. For example, the components need not be in the same room. But in some embodiments, the components are connected to each other in an integral unit. In some embodiments, the same components may perform multiple functions.

Computer Systems and Computer Readable Media

The system, as described in the present technique or any of its components, may be embodied in the form of a computer system. Typical examples of a computer system include a general-purpose computer, a programmed microprocessor, a microcontroller, a peripheral integrated circuit element, and other devices or arrangements of devices that are capable of implementing the steps that constitute the method of the present technique.

A computer system may comprise a computer, an input device, a display unit, and/or the Internet. The computer may further comprise a microprocessor. The microprocessor may be connected to a communication bus. The computer may also include a memory. The memory may include random access memory (RAM) and read only memory (ROM). The computer system may further comprise a storage device. The storage device can be a hard disk drive or a removable storage drive such as a floppy disk drive, optical disk drive, etc. The storage device can also be other similar means for loading computer programs or other instructions into the computer system. The computer system may also include a communication unit. The communication unit allows the computer to connect to other databases and the Internet through an I/O interface. The communication unit allows the transfer to, as well as reception of data from, other databases. The communication unit may include a modem, an Ethernet card, or any similar device which enables the computer system to connect to databases and networks such as LAN, MAN, WAN and the Internet. The computer system thus may facilitate inputs from a user through input device, accessible to the system through I/O interface.

A computing device typically will include an operating system that provides executable program instructions for the general administration and operation of that computing device, and typically will include a computer-readable storage medium (e.g., a hard disk, random access memory, read only memory, etc.) storing instructions that, when executed by a processor of the server, allow the computing device to perform its intended functions. Suitable implementations for the operating system and general functionality of the computing device are known or commercially available, and are readily implemented by persons having ordinary skill in the art, particularly in light of the disclosure herein.

The computer system executes a set of instructions that are stored in one or more storage elements, in order to process input data. The storage elements may also hold data or other information as desired. The storage element may be in the form of an information source or a physical memory element present in the processing machine.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers, or other network devices may be stored locally and/or remotely, as appropriate. Where a system includes computing devices, each such device can include hardware elements that may be electrically coupled via a bus, the elements including, for example, at least one central processing unit (CPU), at least one input device (e.g., a mouse, keyboard, controller, touch screen, or keypad), and at least one output device (e.g., a display device, printer, or speaker). Such a system may also include one or more storage devices, such as disk drives, optical storage devices, and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.), and working memory as described above. The computer-readable storage media reader can be connected with, or configured to receive, a computer-readable storage medium, representing remote, local, fixed, and/or removable storage devices as well as storage media for temporarily and/or more permanently containing, storing, transmitting, and retrieving computer-readable information. The system and various devices also typically will include a number of software applications, modules, services, or other elements located within at least one working memory device, including an operating system and application programs, such as a client application or Web browser. It should be appreciated that alternate embodiments may have numerous variations from that described above. For example, customized hardware might also be used and/or particular elements might be implemented in hardware, software (including portable software, such as applets), or both. Further, connection to other computing devices such as network input/output devices may be employed.

Non-transient storage media and computer readable media for containing code, or portions of code, can include any appropriate media known or used in the art, including storage media and communication media, such as but not limited to volatile and non-volatile, removable and non-removable media implemented in any method or technology for storage and/or transmission of information such as computer readable instructions, data structures, program modules, or other data, including RAM, ROM, EEPROM, flash memory or other memory technology, CD-ROM, digital versatile disk (DVD) or other optical storage, magnetic cassettes, magnetic tape, magnetic disk storage or other magnetic storage devices, or any other medium which can be used to store the desired information and which can be accessed by the a system device. Based on the disclosure and teachings provided herein, a person of ordinary skill in the art will appreciate other ways and/or methods to implement the various embodiments.

A computer-readable medium may comprise, but is not limited to, an electronic, optical, magnetic, or other storage device capable of providing a processor with computer-readable instructions. Other examples include, but are not limited to, a floppy disk, CD-ROM, DVD, magnetic disk, memory chip, ROM, RAM, SRAM, DRAM, content-addressable memory ("CAM"), DDR, flash memory such as NAND flash or NOR flash, an ASIC, a configured processor, optical storage, magnetic tape or other magnetic storage, or any other medium from which a computer processor can read instructions. In one embodiment, the computing device may comprise a single type of computer-readable medium such as random access memory (RAM). In other embodiments, the computing device may comprise two or more types of computer-readable medium such as random access memory (RAM), a disk drive, and cache. The computing device may be in communication with one or more external computer-readable mediums such as an external hard disk drive or an external DVD or Blu-Ray drive.

As discussed above, the embodiment comprises a processor which is configured to execute computer-executable program instructions and/or to access information stored in memory. The instructions may comprise processor-specific instructions generated by a compiler and/or an interpreter from code written in any suitable computer-programming language including, for example, C, C++, C#, Visual Basic, Java, Python, Perl, JavaScript, and ActionScript (Adobe Systems, Mountain View, Calif). In an embodiment, the computing device comprises a single processor. In other embodiments, the device comprises two or more processors. Such processors may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

The computing device comprises a network interface. In some embodiments, the network interface is configured for communicating via wired or wireless communication links. For example, the network interface may allow for communication over networks via Ethernet, IEEE 802.11 (Wi-Fi), 802.16 (Wi-Max), Bluetooth, infrared, etc. As another example, network interface may allow for communication over networks such as CDMA, GSM, UMTS, or other cellular communication networks. In some embodiments, the network interface may allow for point-to-point connections with another device, such as via the Universal Serial Bus (USB), 1394 FireWire, serial or parallel connections, or similar interfaces. Some embodiments of suitable computing devices may comprise two or more network interfaces for communication over one or more networks. In some embodiments, the computing device may include a data store in addition to or in place of a network interface.

Some embodiments of suitable computing devices may comprise or be in communication with a number of external or internal devices such as a mouse, a CD-ROM, DVD, a keyboard, a display, audio speakers, one or more microphones, or any other input or output devices. For example, the computing device may be in communication with various user interface devices and a display. The display may use any suitable technology including, but not limited to, LCD, LED, CRT, and the like.

The set of instructions for execution by the computer system may include various commands that instruct the processing machine to perform specific tasks such as the steps that constitute the method of the present technique. The set of instructions may be in the form of a software program. Further, the software may be in the form of a collection of separate programs, a program module with a larger program or a portion of a program module, as in the present technique. The software may also include modular programming in the form of object-oriented programming. The processing of input data by the processing machine may be in response to user commands, results of previous processing, or a request made by another processing machine.

While the present invention has been disclosed with references to certain embodiments, numerous modifications, alterations and changes to the described embodiments are possible without departing from the scope and spirit of the present invention, as defined in the appended claims. Accordingly, it is intended that the present invention not be limited to the described embodiments, but that it have the full scope defined by the language of the following claims, and equivalents thereof.

EXAMPLES

Results depicted in the following examples demonstrate detection of a low number of cells, even a single bacterium, in a shortened time to results.

Example 1

Creation and Isolation of Indicator Phage from *Salmonella*.-Specific Bacteriophage Indicator phage *Salmonella*-specific SEA1.NANOLUC®TSP1.NANOLUC® bacteriophage were created through homologous recombination using procedures as previously described. *Salmonella* phage TSP1 and TSP11 were isolated from sewage samples.

The genomic sequences of these phage were obtained through whole genome sequencing using the Illumina MiSeq system with de novo sequence assembly. Based on previously known and annotated genomes of related phage, the late gene regions and Major Capsid Protein genes were located on the new phage genomes. Plasmids were designed and synthesized to insert NANOLUC® along with the appropriate late gene promoter and ribosomal binding site, flanked by approximately 500 bp of matching phage sequence to promote homologous recombination.

Target bacteria were transformed with the Homologous Recombination Plasmids under appropriate antibiotic selection and infected with their respective wild-type phage to allow for homologous recombination with the plasmid. Following homologous recombination to generate the recombinant bacteriophage genomes, a series of titer and enrichment steps was used to isolate specific recombinant bacteriophages that express NANOLUC® as previously described.

Finally, large-scale production was performed to obtain high titer stocks appropriate for use in the *Salmonella* spp. detection assays. Cesium chloride isopycnic density gradient centrifugation was used to separate phage particles from contaminating luciferase protein to reduce background.

Example 2

Bacterial Detection Using *Salmonella*-Specific Bacteriophage NANOLUC® Indicator Phage after Incubation of Sample in Media Detection of *Salmonella* spp. using the *Salmonella*-specific bacteriophage NANOLUC® indicator phage was tested in experiments using the assay format embodiment depicted in FIG. 7. First, cell numbers ranging from 1-10,000 were taken from cultures and infected with $10^5$, $10^6$, and $10^7$ phage/mL in identical sample volumes of LB for 2, hours. Following the addition of lysis buffer and NANO-GLO® reagent, the reaction was read using a GLOMAX® 96 instrument. These experiments demonstrated that the optimal assay for any particular target pathogen can vary, based on the sample type and size, the microorganism to be detected, and the specific bacteriophage used to create the recombinant indicator phage.

Example 3

*Salmonella* Detection in Ground Raw Turkey or Chicken Samples

*Salmonella* can be detected in food samples or environmental samples where the food is procesed, e.g., turkey or chicken processing facilities using. 25 g samples of ground turkey or chicken were uninoculated, inoculated at a low level (0.2-2.0 CFU/sample) or inoculated at a high level (2-10 CFU/sample). Inoculated samples were stored at 4° C. for 48-72 hours before assay was performed. Each test sample was mixed with 75 mL of pre-warmed (41° C.) tryptone soy broth (TSB) media for a 1:3 sample:volume ratio. The STOMACHER®, a peristaltic blender, or equivalent, was used to homogenize the sample at highest setting for 30 seconds. The homogenized sample was incubated at 41° C. for 5, 6, and 7 hours. Bags containing the samples were gently massaged to thoroughly mix contents. Following incubation, 2 mL of sample was removed and transferred to a culture tube. The sample was divided into 150 µL and 1 mL samples. The 150 µL samples were transferred to a 96-well plate. 10 µl of $1.2\times10^7$ P/mL of appropriate bacteriophage cocktail solution was added to each well and incubated for 2 hours at 37° C. 65 µL of NANO-GLO® Master Mix was added to each sample and samples were read on a GLOMAX 96® luminometer. The 1 mL samples were centrifuged on the highest setting for 1 min. Supernatants were removed and discarded and the pellet was resuspended in 200 µL of pre-warmed (41° C.) TSB. 15 µl of $1.2\times10^7$ P/mL of *Salmonella* spp. bacteriophage cocktail solution was added to each sample, gently mixed, and incubated for 2 hours at 37° C. 65 µL of NANOGLO® Master Mix was added to each sample and then briefly vortexed in microfuge tubes. Samples were then centrifuged for 5-10 seconds to pellet debris. 215 µL of sample was transferred to the 96-well plate without disturbing the debris pellet and samples were read on a GLOMAX 96® luminometer. A signal/background ratio ≥750 RLU indicated positive detection of *Salmonella* spp. A signal/background ratio of <750 RLU indicated the sample was negative for *Salmonella* spp.

Positive detection of *Salmonella* spp. was confirmed. Samples were enriched for 20-24 hours at 37° C. 1 mL of sample was then put through IMS bead selection and plated on a chromogenic selection plate specific for *Salmonella* spp. With 6 hours of enrichment, the assay detected all positives for both 150 µL and 1 mL samples. 5 hour enrichment was sufficient for detection with 1 mL samples.

TABLE 1

Ground Turkey *Salmonella* spp. Assay (150 µL sample)

| 150 µl Sample | | | 5 hr Enrichment | | | 6 hr Enrichment | | | 7 hr Enrichment | | |
| --- | --- | --- | --- | --- | --- | --- | --- | --- | --- | --- | --- |
| Sample | Target Est. Spike | CFU | 5 hr RLU | 5 hr Signal/Background | 5 hr Result | 6 hr RLU | 6 hr Signal/Background | 6 hr Result | 7 hr RLU | 7 hr Signal/Background | 7 hr Result |
| 2 | UNINOC | 0.0 | 271 | 1.1 | NEG | 287 | 1.1 | NEG | 275 | 1.1 | NEG |
| 16 | UNINOC | 0.0 | 325 | 1.3 | NEG | 265 | 1.1 | NEG | 281 | 1.1 | NEG |
| 18 | UNINOC | 0.0 | 170 | 0.7 | NEG | 206 | 0.8 | NEG | 199 | 0.8 | NEG |
| 21 | UNINOC | 0.0 | 213 | 0.9 | NEG | 225 | 0.9 | NEG | 234 | 0.9 | NEG |
| 23 | UNINOC | 0.0 | 180 | 0.7 | NEG | 227 | 0.9 | NEG | 242 | 1.0 | NEG |
| 1 | LOW | 1.2 | 4495 | 18.0 | POS | 37901 | 151.6 | POS | 442600 | 1770.4 | POS |
| 3 | LOW | 1.2 | 259 | 1.0 | NEG | 271 | 1.1 | NEG | 315 | 1.3 | NEG |
| 5 | LOW | 1.2 | 1374 | 5.5 | POS | 30339 | 121.4 | POS | 494142 | 1976.6 | POS |
| 6 | LOW | 1.2 | 10083 | 40.3 | POS | 60839 | 243.4 | POS | 799280 | 3197.1 | POS |
| 7 | LOW | 1.2 | 18226 | 72.9 | POS | 170117 | 680.5 | POS | 1958573 | 7834.3 | POS |
| 8 | LOW | 1.2 | 11250 | 45.0 | POS | 121831 | 487.3 | POS | 1505752 | 6023.0 | POS |
| 10 | LOW | 1.2 | 1804 | 7.2 | POS | 17638 | 70.6 | POS | 193210 | 772.8 | POS |
| 11 | LOW | 1.2 | 314 | 1.3 | NEG | 277 | 1.1 | NEG | 225 | 0.9 | NEG |
| 12 | LOW | 1.2 | 6419 | 25.7 | POS | 52125 | 208.5 | POS | 412072 | 1648.3 | POS |
| 14 | LOW | 1.2 | 3614 | 14.5 | POS | 23002 | 92.0 | POS | 258488 | 1034.0 | POS |
| 15 | LOW | 1.2 | 289 | 1.2 | NEG | 284 | 1.1 | NEG | 317 | 1.3 | NEG |
| 17 | LOW | 1.2 | 249 | 1.0 | NEG | 230 | 0.9 | NEG | 192 | 0.8 | NEG |
| 19 | LOW | 1.2 | 215 | 0.9 | NEG | 3234 | 12.9 | POS | 29750 | 119.0 | POS |
| 20 | LOW | 1.2 | 2230 | 8.9 | POS | 19960 | 79.8 | POS | 267300 | 1069.2 | POS |
| 22 | LOW | 1.2 | 3970 | 15.9 | POS | 13770 | 55.1 | POS | 185500 | 742.0 | POS |
| 24 | LOW | 1.2 | 4069 | 16.3 | POS | 32942 | 131.8 | POS | 461179 | 1844.7 | POS |
| 25 | LOW | 1.2 | 251 | 1.0 | NEG | 218 | 0.9 | NEG | 227 | 0.9 | NEG |
| 26 | LOW | 1.2 | 4132 | 16.5 | POS | 34069 | 136.3 | POS | 344198 | 1376.8 | POS |

TABLE 1-continued

Ground Turkey *Salmonella* spp. Assay (150 µL sample)

| 150 µl Sample | | | 5 hr Enrichment | | | 6 hr Enrichment | | | 7 hr Enrichment | | |
|---|---|---|---|---|---|---|---|---|---|---|---|
| Sample | Target Est. Spike | CFU | 5 hr RLU | 5 hr Signal/ Background | 5 hr Result | 6 hr RLU | 6 hr Signal/ Background | 6 hr Result | 7 hr RLU | 7 hr Signal/ Background | 7 hr Result |
| 28 | LOW | 1.2 | 191 | 0.8 | NEG | 235 | 0.9 | NEG | 208 | 0.8 | NEG |
| 30 | LOW | 1.2 | 267 | 1.1 | NEG | 280 | 1.1 | NEG | 311 | 1.2 | NEG |
| 4 | HIGH | 6.1 | 46170 | 184.7 | POS | 322398 | 1289.6 | POS | 4328205 | 17312.8 | POS |
| 9 | HIGH | 6.1 | 30905 | 123.6 | POS | 361609 | 1446.4 | POS | 5480287 | 21921.1 | POS |
| 13 | HIGH | 6.1 | 40088 | 160.4 | POS | 441490 | 1766.0 | POS | 5738016 | 22952.1 | POS |
| 27 | HIGH | 6.1 | 2444 | 9.8 | POS | 31854 | 127.4 | POS | 348080 | 1392.3 | POS |
| 29 | HIGH | 6.1 | 10098 | 40.4 | POS | 65018 | 260.1 | POS | 809694 | 3238.8 | POS |

TABLE 2

Ground Turkey *Salmonella* spp. Assay (1 mL sample)

| 1 mL Concentrated Sample | | | 5 hr Enrichment | | | 6 hr Enrichment | | | 7 hr Enrichment | | |
|---|---|---|---|---|---|---|---|---|---|---|---|
| Sample | Spike Level | CFU | 5 hr RLU | 5 hr Signal/ Background | 5 hr Result | 6 hr RLU | 6 hr Signal/ Background | 6 hr Result | 7 hr RLU | 7 hr Signal/ Background | 7 hr Result |
| 2 | UNINOC | 0.0 | 109 | 0.4 | NEG | 101 | 0.4 | NEG | 121 | 0.5 | NEG |
| 16 | UNINOC | 0.0 | 231 | 0.9 | NEG | 174 | 0.7 | NEG | 141 | 0.6 | NEG |
| 18 | UNINOC | 0.0 | 101 | 0.4 | NEG | 104 | 0.4 | NEG | 57 | 0.2 | NEG |
| 21 | UNINOC | 0.0 | 128 | 0.5 | NEG | 69 | 0.3 | NEG | 69 | 0.3 | NEG |
| 23 | UNINOC | 0.0 | 194 | 0.8 | NEG | 84 | 0.3 | NEG | 68 | 0.3 | NEG |
| 1 | LOW | 1.2 | 6313 | 25.3 | POS | 59524 | 238.1 | POS | 1148437 | 4593.7 | POS |
| 3 | LOW | 1.2 | 142 | 0.6 | NEG | 112 | 0.4 | NEG | 118 | 0.5 | NEG |
| 5 | LOW | 1.2 | 7822 | 31.3 | POS | 131381 | 525.5 | POS | 1337166 | 5348.7 | POS |
| 6 | LOW | 1.2 | 14092 | 56.4 | POS | 83108 | 332.4 | POS | 3513244 | 14053.0 | POS |
| 7 | LOW | 1.2 | 37321 | 149.3 | POS | 350051 | 1400.2 | POS | 3406812 | 13627.2 | POS |
| 8 | LOW | 1.2 | 15762 | 63.0 | POS | 168150 | 672.6 | POS | 1863963 | 7455.9 | POS |
| 10 | LOW | 1.2 | 6365 | 25.5 | POS | 55887 | 223.5 | POS | 594467 | 2377.9 | POS |
| 11 | LOW | 1.2 | 135 | 0.5 | NEG | 162 | 0.6 | NEG | 110 | 0.4 | NEG |
| 12 | LOW | 1.2 | 15946 | 63.8 | POS | 108686 | 434.7 | POS | 1553574 | 6214.3 | POS |
| 14 | LOW | 1.2 | 2824 | 11.3 | POS | 82837 | 331.3 | POS | 638513 | 2554.1 | POS |
| 15 | LOW | 1.2 | 134 | 0.5 | NEG | 177 | 0.7 | NEG | 140 | 0.6 | NEG |
| 17 | LOW | 1.2 | 121 | 0.5 | NEG | 94 | 0.4 | NEG | 71 | 0.3 | NEG |
| 19 | LOW | 1.2 | 1280 | 5.1 | POS | 7393 | 29.6 | POS | 97380 | 389.5 | POS |
| 20 | LOW | 1.2 | 8758 | 35.0 | POS | 95480 | 381.9 | POS | 1168000 | 4672.0 | POS |
| 22 | LOW | 1.2 | 9690 | 38.8 | POS | 58400 | 233.6 | POS | 702400 | 2809.6 | POS |
| 24 | LOW | 1.2 | 8903 | 35.6 | POS | 66413 | 265.7 | POS | 385008 | 1540.0 | POS |
| 25 | LOW | 1.2 | 120 | 0.5 | NEG | 79 | 0.3 | NEG | 76 | 0.3 | NEG |
| 26 | LOW | 1.2 | 3360 | 13.4 | POS | 81605 | 326.4 | POS | 1539384 | 6157.5 | POS |
| 28 | LOW | 1.2 | 122 | 0.5 | NEG | 149 | 0.6 | NEG | 106 | 0.4 | NEG |
| 30 | LOW | 1.2 | 164 | 0.7 | NEG | 65 | 0.3 | NEG | 134 | 0.5 | NEG |
| 4 | HIGH | 6.1 | 47888 | 191.6 | POS | 1345672 | 5382.7 | POS | 8551625 | 34206.5 | POS |
| 9 | HIGH | 6.1 | 150225 | 600.9 | POS | 1572399 | 6289.6 | POS | 24842200 | 99368.8 | POS |
| 13 | HIGH | 6.1 | 105337 | 421.3 | POS | 677351 | 2709.4 | POS | 16348527 | 65394.1 | POS |
| 27 | HIGH | 6.1 | 4282 | 17.1 | POS | 68369 | 273.5 | POS | 1178443 | 4713.8 | POS |
| 29 | HIGH | 6.1 | 5311 | 21.2 | POS | 197412 | 789.6 | POS | 4135790 | 16543.2 | POS |

TABLE 3

Ground Turkey *Salmonella* spp. Assay

| 1 mL Concentrated Sample | | | 5 hr Enrichment | | | 6 hr Enrichment | | | 7 hr Enrichment | | |
|---|---|---|---|---|---|---|---|---|---|---|---|
| Sample | Spike Level | CFU | 5 hr RLU | 5 hr Signal/ Background | 5 hr Result | 6 hr RLU | 6 hr Signal/ Background | 6 hr Result | 7 hr RLU | 7 hr Signal/ Background | 7 hr Result |
| 2 | UNINOC | 0.0 | 109 | 0.4 | NEG | 101 | 0.4 | NEG | 121 | 0.5 | NEG |
| 16 | UNINOC | 0.0 | 231 | 0.9 | NEG | 174 | 0.7 | NEG | 141 | 0.6 | NEG |
| 18 | UNINOC | 0.0 | 101 | 0.4 | NEG | 104 | 0.4 | NEG | 57 | 0.2 | NEG |
| 21 | UNINOC | 0.0 | 128 | 0.5 | NEG | 69 | 0.3 | NEG | 69 | 0.3 | NEG |
| 23 | UNINOC | 0.0 | 194 | 0.8 | NEG | 84 | 0.3 | NEG | 68 | 0.3 | NEG |
| 1 | LOW | 1.2 | 6313 | 25.3 | POS | 59524 | 238.1 | POS | 1148437 | 4593.7 | POS |
| 3 | LOW | 1.2 | 142 | 0.6 | NEG | 112 | 0.4 | NEG | 118 | 0.5 | NEG |
| 5 | LOW | 1.2 | 7822 | 31.3 | POS | 131381 | 525.5 | POS | 1337166 | 5348.7 | POS |
| 6 | LOW | 1.2 | 14092 | 56.4 | POS | 83108 | 332.4 | POS | 3513244 | 14053.0 | POS |
| 7 | LOW | 1.2 | 37321 | 149.3 | POS | 350051 | 1400.2 | POS | 3406812 | 13627.2 | POS |
| 8 | LOW | 1.2 | 15762 | 63.0 | POS | 168150 | 672.6 | POS | 1863963 | 7455.9 | POS |

TABLE 3-continued

Ground Turkey Salmonella spp. Assay

| | | | 5 hr Enrichment | | | 6 hr Enrichment | | | 7 hr Enrichment | | |
|---|---|---|---|---|---|---|---|---|---|---|---|
| 1 mL Concentrated Sample | | | | | | | | | | | |
| Sample | Spike Level | CFU | 5 hr RLU | 5 hr Signal/ Background | 5 hr Result | 6 hr RLU | 6 hr Signal/ Background | 6 hr Result | 7 hr RLU | 7 hr Signal/ Background | 7 hr Result |
| 10 | LOW | 1.2 | 6365 | 25.5 | POS | 55887 | 223.5 | POS | 594467 | 2377.9 | POS |
| 11 | LOW | 1.2 | 135 | 0.5 | NEG | 162 | 0.6 | NEG | 110 | 0.4 | NEG |
| 12 | LOW | 1.2 | 15946 | 63.8 | POS | 108686 | 434.7 | POS | 1553574 | 6214.3 | POS |
| 14 | LOW | 1.2 | 2824 | 11.3 | POS | 82837 | 331.3 | POS | 638513 | 2554.1 | POS |
| 15 | LOW | 1.2 | 134 | 0.5 | NEG | 177 | 0.7 | NEG | 140 | 0.6 | NEG |
| 17 | LOW | 1.2 | 121 | 0.5 | NEG | 94 | 0.4 | NEG | 71 | 0.3 | NEG |
| 19 | LOW | 1.2 | 1280 | 5.1 | POS | 7393 | 29.6 | POS | 97380 | 389.5 | POS |
| 20 | LOW | 1.2 | 8758 | 35.0 | POS | 95480 | 381.9 | POS | 1168000 | 4672.0 | POS |
| 22 | LOW | 1.2 | 9690 | 38.8 | POS | 58400 | 233.6 | POS | 702400 | 2809.6 | POS |
| 24 | LOW | 1.2 | 8903 | 35.6 | POS | 66413 | 265.7 | POS | 385008 | 1540.0 | POS |
| 25 | LOW | 1.2 | 120 | 0.5 | NEG | 79 | 0.3 | NEG | 76 | 0.3 | NEG |
| 26 | LOW | 1.2 | 3360 | 13.4 | POS | 81605 | 326.4 | POS | 1539384 | 6157.5 | POS |
| 28 | LOW | 1.2 | 122 | 0.5 | NEG | 149 | 0.6 | NEG | 106 | 0.4 | NEG |
| 30 | LOW | 1.2 | 164 | 0.7 | NEG | 65 | 0.3 | NEG | 134 | 0.5 | NEG |
| 4 | HIGH | 6.1 | 47888 | 191.6 | POS | 1345672 | 5382.7 | POS | 8551625 | 34206.5 | POS |
| 9 | HIGH | 6.1 | 150225 | 600.9 | POS | 1572399 | 6289.6 | POS | 24842200 | 99368.8 | POS |
| 13 | HIGH | 6.1 | 105337 | 421.3 | POS | 677351 | 2709.4 | POS | 16348527 | 65394.1 | POS |
| 27 | HIGH | 6.1 | 4282 | 17.1 | POS | 68369 | 273.5 | POS | 1178443 | 4713.8 | POS |
| 29 | HIGH | 6.1 | 5311 | 21.2 | POS | 197412 | 789.6 | POS | 4135790 | 16543.2 | POS |

Example 4

Salmonella Detection in Dog Food Samples

Dog food samples were uninoculated, inoculated at a low level (0.2-2.0 CFU/sample) or inoculated at a high level (2-10 CFU/sample). Inoculated samples were stored at 4° C. for >24 hours before assay was performed.

25 g of dog food sample was mixed with 225 mL of pre-warmed (41° C.) lactose broth or TSB media for a 1:9 sample:volume ratio. The sample was incubated at 41° C. for 30 minutes to allow the sample to soften. The STOM-ACHER®, a peristaltic blender, or an equivalent, was used to homogenize the sample at highest setting for 60 seconds. The homogenized sample was incubated at 41° C. without shaking for 16-18 hours. The bag containing the sample was gently massaged/shaken to thoroughly mix contents. 1 mL of sample was removed and the culture was diluted 1:10 in TSB (100 µL sample: 900 µL TSB). 150 µL of dilution sample was then transferred to a 96-well black plate. 10 µl of bacteriophage cocktail of Salmonella-specific bacteriophage solution was added to each well and incubated for 2 hours at 37° C. NANOGLO® Master Mix reagent was prepared and 65 µL of reagent was added to each well and gently mixed my pipetting up and down. Following 3 minutes of incubation after substrate addition, samples were read on a GLOMAX 96® luminometer.

Positive detection of Salmonella spp. was confirmed. Samples were enriched for 24 hours at 41° C. 1 mL of overnight culture was removed and the anti-Salmonella spp. DYNABEADS® procedure was followed according to the manufacturer's instructions. Following IMS bead selection, beads were resuspended in 100 µL of PBS and plated on a chromogenic selection plate specific for Salmonella spp. Plates were incubated for 18-24 hours at 37° C.±1° C. The presence of mauve colonies confirmed the presence of Salmonella spp.

As shown in Table 5, the dog food Salmonella spp. assay had no false positives or false negatives.

TABLE 5

Dog Food Salmonella spp. Assay

| Sample | Spike Level | RLU | Signal-Background | Signal/Background | Phage Assay Result | Confirmation Assay |
|---|---|---|---|---|---|---|
| 7 | uninoc | 48 | −202 | 0.2 | NEG | NEG |
| 12 | uninoc | 54 | −196 | 0.2 | NEG | NEG |
| 17 | uninoc | 49 | −201 | 0.2 | NEG | NEG |
| 22 | uninoc | 52 | −198 | 0.2 | NEG | NEG |
| 27 | uninoc | 45 | −205 | 0.2 | NEG | NEG |
| 1 | low | 42370000 | 42369750 | 169480.0 | POS | POS |
| 2 | low | 43170000 | 43169750 | 172680.0 | POS | POS |
| 3 | low | 70180000 | 70179750 | 280720.0 | POS | POS |
| 4 | low | 29350000 | 29349750 | 117400.0 | POS | POS |
| 5 | low | 37 | −213 | 0.1 | NEG | NEG |
| 6 | low | 39 | −211 | 0.2 | NEG | NEG |
| 8 | low | 20890000 | 20889750 | 83560.0 | POS | POS |
| 10 | low | 3224000 | 3223750 | 12896.0 | POS | POS |
| 11 | low | 60 | −190 | 0.2 | NEG | NEG |
| 13 | low | 5532839 | 5532589 | 22131.4 | POS | POS |
| 15 | low | 73101712 | 73101462 | 292406.8 | POS | POS |
| 16 | low | 2082342 | 2082092 | 8329.4 | POS | POS |
| 18 | low | 10373953 | 10373703 | 41495.8 | POS | POS |

TABLE 5-continued

| | | | | | | |
|---|---|---|---|---|---|---|
| Sample | Spike Level | RLU | Signal-Background | Signal/Background | Phage Assay Result | Confirmation Assay |
| 20 | low | 47052716 | 47052466 | 188210.9 | POS | POS |
| 21 | low | 51 | −199 | 0.2 | NEG | NEG |
| 23 | low | 44243100 | 44242850 | 176972.4 | POS | POS |
| 25 | low | 14358209 | 14357959 | 57432.8 | POS | POS |
| 26 | low | 37 | −213 | 0.1 | NEG | NEG |
| 28 | Low | 45 | −205 | 0.2 | NEG | NEG |
| 30 | Low | 28358970 | 28358720 | 113435.9 | POS | POS |
| 9 | High | 8596000 | 8595750 | 34384.0 | POS | POS |
| 14 | High | 26649364 | 26649114 | 106597.5 | POS | POS |
| 19 | High | 39769272 | 39769022 | 159077.1 | POS | POS |
| 24 | High | 16702595 | 16702345 | 66810.4 | POS | POS |
| 29 | High | 162177760 | 162177510 | 648711.0 | POS | POS |

Example 5

Salmonella Detection in Powdered Infant Formula

Samples were inoculated with Salmonella dried in PIF at various inoculation levels; uninoculated, low inoculation (0.2-2 CFU/sample) or high inoculation (2-10 CFU/sample). Inoculated samples were allowed to sit at room temperature for 2-4 weeks before assays were performed.

10 g, 100 g, and 300 g samples of test PIF were prepared. 10 g of PIF sample was mixed with 90 mL of pre-warmed (37° C.). buffered peptone water (BPW) media for a 1:9 sample:volume ratio; 100 g of PIF was mixed with 300 mL of pre-warmed BPW media for 1:3 sample:volume ratio; and 300 g of PIF was mixed with 900 mL of pre-warmed BPW media for 1:3 sample:volume ratio. The STOMACHER®, a peristaltic blender, or an equivalent, was used to homogenize the sample at highest setting for 120 seconds. The homogenized sample was incubated at 37° C. without shaking for 16-18 hours. The bag containing the sample was gently massaged/shaken to thoroughly mix contents. 1 mL of sample was removed and the culture was diluted 1:10 in BPW (100 μL sample: 900 μL BPW). 150 μL of dilution sample was then transferred to a 96-well black plate. 10 μl of bacteriophage cocktail of Salmonella-specific bacteriophage solution was added to each well and incubated for 2 hours at 37° C. NANOGLO® Master Mix reagent was prepared and 65 μL of reagent was added to each well and gently mixed my pipetting up and down. Following 3 minutes of incubation after substrate addition, samples were read on a GLOMAX 96® luminometer.

Positive detection of Salmonella spp. was confirmed. Samples were enriched for 24 hours at 37° C. 1 mL of overnight culture was removed and the anti-Salmonella DYNABEADS® procedure was followed according to the manufacturer's instructions. Following IMS bead selection, beads were resuspended in 100 μL of PBS and plated on a chromogenic selection plate specific for Salmonella. Plates were incubated for 18-24 hours at 37° C.±1° C. The presence of mauve colonies confirmed the presence of Salmonella.

As shown in Table 6, the PIF Salmonella assay had no false positives or false negatives.

TABLE 6

PIF Salmonella spp. Assay (10 g)

| Sample | Spike Level | SEA1/TSP1 RLU | SEA1/TSP1 Signal - Background | SEA1/TSP1 Signal/Background | Phage Assay Result | Confirmation Plate |
|---|---|---|---|---|---|---|
| 2 | uninoc | 92 | −158 | 0.4 | NEG | NEG |
| 11 | uninoc | 106 | −144 | 0.4 | NEG | NEG |
| 12 | uninoc | 112 | −138 | 0.4 | NEG | NEG |
| 21 | uninoc | 1371 | 1121 | 5.5 | NEG* | NEG |
| 5 | low | 95 | −155 | 0.4 | NEG | NEG |
| 6 | low | 96 | −154 | 0.4 | NEG | NEG |
| 7 | low | 32420000 | 32419750 | 129680.0 | POS | POS |
| 8 | low | 12750000 | 12749750 | 51000.0 | POS | POS |
| 9 | low | 61 | −189 | 0.2 | NEG | NEG |
| 10 | low | 8658000 | 8657750 | 34632.0 | POS | POS |
| 15 | low | 13355638 | 13355388 | 53422.6 | POS | POS |
| 16 | low | 34743668 | 34743418 | 138974.7 | POS | POS |
| 17 | low | 113 | −137 | 0.5 | NEG | NEG |
| 18 | low | 83 | −167 | 0.3 | NEG | NEG |
| 19 | low | 33121322 | 33121072 | 132485.3 | POS | POS |
| 20 | low | 112 | −138 | 0.4 | NEG | NEG |
| 23 | low | 19638814 | 19638564 | 78555.3 | POS | POS |
| 24 | low | 5189561 | 5189311 | 20758.2 | POS | POS |
| 25 | low | 29838676 | 29838426 | 119354.7 | POS | POS |
| 26 | low | 115 | −135 | 0.5 | NEG | NEG |
| 27 | low | 15562075 | 15561825 | 62248.3 | POS | POS |
| 28 | low | 117 | −133 | 0.5 | NEG | NEG |
| 29 | low | 10624720 | 10624470 | 42498.9 | POS | POS |
| 30 | low | 97 | −153 | 0.4 | NEG | NEG |
| 3 | high | 17780000 | 17779750 | 71120.0 | POS | POS |

TABLE 6-continued

| | | PIF *Salmonella* spp. Assay (10 g) | | | | |
|---|---|---|---|---|---|---|
| Sample | Spike Level | SEA1/TSP1 RLU | SEA1/TSP1 Signal - Background | SEA1/TSP1 Signal/ Background | Phage Assay Result | Confirmation Plate |
| 4 | high | 24500000 | 24499750 | 98000.0 | POS | POS |
| 13 | high | 22195220 | 22194970 | 88780.9 | POS | POS |
| 14 | high | 26651412 | 26651162 | 106605.6 | POS | POS |
| 22 | high | 26835974 | 26835724 | 107343.9 | POS | POS |

*Accidental splash when loading plate

Example 6

*Salmonella* Detection in Milk Samples

Samples were inoculated with *Salmonella* at various inoculation levels; uninoculated, low inoculation (0.2-2 CFU/sample) or high inoculation (2-10 CFU/sample). Inoculated samples were allowed to sit at 4° C. for 48-72 hours before assays were performed.

25 mL of milk sample was mixed with 75 mL of pre-warmed (41° C.) media for a 1:3 sample:volume ratio. The STOMACHER®, a peristaltic blender, or an equivalent, was used to homogenize the sample at highest setting for 60 seconds. The homogenized sample was incubated at 41° C. without shaking for 5, 6, or 7 hours. The bag containing the sample was gently massaged/shaken to thoroughly mix contents. 1 mL of sample was removed and centrifuged on the highest setting for 1 minute. The supernatant was removed and the pellet was resuspended in 200 µL of pre-warmed media. 15 µl of bacteriophage cocktail of *Salmonella*-specific bacteriophage solution was added to each well and incubated for 2 hours at 37° C. Samples were vortexed and then centrifuged for 5-10 seconds to pellet debris. 150 µL of sample was transferred to a 96 well plate. NANOGLO® Master Mix reagent was prepared and 65 µL of reagent was added to each well and gently mixed my pipetting up and down. Following 3 minutes of incubation after substrate addition, samples were read on a GLOMAX 96® luminometer.

Positive detection of *Salmonella* was confirmed. Samples were enriched for 18-24 hours total at 41° C. 1 mL of overnight culture was removed and the anti-*Salmonella* DYNABEADS® procedure was followed according to the manufacturer's instructions. Following IMS bead selection, beads were resuspended in 100 µL of PBS and plated on a chromogenic selection plate specific for *Salmonella* spp. Plates were incubated for 18-24 hours at 37° C.±1° C. The presence of mauve colonies confirmed the presence of *Salmonella* spp.

Positive detection of *Salmonella* spp. was indicated by >750 RLU or a signal:background >3.0. Background detection was determined to be 250 RLU. As shown in Table 7, the milk *Salmonella* spp. assay had no false positives or false negatives following 6 or 7 hours of enrichment. Following 5 hours of enrichment, samples 12, 13, 15, 18, and 25 produced false negatives.

TABLE 7

| | | | Milk *Salmonella enterica* Assay | | | | | | | | | | | |
|---|---|---|---|---|---|---|---|---|---|---|---|---|---|---|
| | | | 5 hr Enrichment | | | 6 hr Enrichment | | | 7 hr Enrichment | | | Overnight Enrichment | | |
| | | | 5 hr | 5 hr | 5 hr | 6 hr | 6 hr | 6 hr | 7 hr | 7 hr | 7 hr | | | |
| | 1 mL Sample | | 1 mL | 1 mL | 1 mL | 1 mL | 1 mL | 1 mL | 1 mL | 1 mL | 1 mL | O/N | O/N | O/N |
| Sample | Target Est. Spike | CFU | Conc. RLU | Conc. S/B | Conc. RLU | Conc. RLU | Conc. S/B | Conc. RLU | Conc. RLU | Conc. S/B | Conc. RLU | 1:10 RLU | 1:10 S/B | 1:10 Result |
| 4 | 0 | 0 | 233 | 0.9 | NEG | 253 | 1.0 | NEG | 222 | 0.9 | NEG | 5101 | 20.4 | NEG |
| 10 | 0 | 0 | 283 | 1.1 | NEG | 260 | 1.0 | NEG | 244 | 1.0 | NEG | 29772 | 119.1 | NEG |
| 14 | 0 | 0 | 221 | 0.9 | NEG | 234 | 0.9 | NEG | 248 | 1.0 | NEG | 18399 | 73.6 | NEG |
| 20 | 0 | 0 | 237 | 0.9 | NEG | 210 | 0.8 | NEG | 289 | 1.2 | NEG | 38495 | 154.0 | NEG |
| 24 | 0 | 0 | 261 | 1.0 | NEG | 250 | 1.0 | NEG | 227 | 0.9 | NEG | 16393 | 65.6 | NEG |
| 2 | 1 | 1.2 | 2549 | 10.2 | POS | 2262 | 9.0 | POS | 36127 | 144.5 | POS | 404572832 | 1618291.3 | POS |
| 3 | 1 | 1.2 | 263 | 1.1 | NEG | 236 | 0.9 | NEG | 282 | 1.1 | NEG | 6871 | 27.5 | NEG |
| 5 | 1 | 1.2 | 259 | 1.0 | NEG | 1337 | 5.3 | POS | 5941 | 23.8 | POS | 418737280 | 1674949.1 | POS |
| 7 | 1 | 1.2 | 272 | 1.1 | NEG | 250 | 1.0 | NEG | 283 | 1.1 | NEG | 35242 | 141.0 | NEG |
| 8 | 1 | 1.2 | 1625 | 6.5 | POS | 4945 | 19.8 | POS | 26059 | 104.2 | POS | 316705536 | 1266822.1 | POS |
| 12 | 1 | 1.2 | 262 | 1.0 | NEG | 1227 | 4.9 | POS | 8038 | 32.2 | POS | 186169600 | 744678.4 | POS |
| 13 | 1 | 1.2 | 223 | 0.9 | NEG | 2426 | 9.7 | POS | 8020 | 32.1 | POS | 54255396 | 217021.6 | POS |
| 15 | 1 | 1.2 | 716 | 2.9 | NEG | 2404 | 9.6 | POS | 16143 | 64.6 | POS | 171687376 | 686749.5 | POS |
| 17 | 1 | 1.2 | 243 | 1.0 | NEG | 240 | 1.0 | NEG | 295 | 1.2 | NEG | 15296 | 61.2 | NEG |
| 18 | 1 | 1.2 | 580 | 2.3 | NEG | 835 | 3.3 | POS | 3167 | 12.7 | POS | 293230144 | 1172920.6 | POS |
| 22 | 1 | 1.2 | 231 | 0.9 | NEG | 255 | 1.0 | NEG | 265 | 1.1 | NEG | 46475 | 185.9 | NEG |
| 23 | 1 | 1.2 | 908 | 3.6 | POS | 948 | 3.8 | POS | 2726 | 10.9 | POS | 197835408 | 791341.6 | POS |
| 25 | 1 | 1.2 | 665 | 2.7 | NEG | 1802 | 7.2 | POS | 6127 | 24.5 | POS | 24409542 | 97638.2 | POS |
| 27 | 1 | 1.2 | 1430 | 5.7 | POS | 3212 | 12.8 | POS | 20179 | 80.7 | POS | 213923536 | 855694.1 | POS |
| 28 | 1 | 1.2 | 250 | 1.0 | NEG | 264 | 1.1 | NEG | 269 | 1.1 | NEG | 14175 | 56.7 | NEG |
| 1 | 10 | 12.0 | 4875 | 19.5 | POS | 15338 | 61.4 | POS | 139098 | 556.4 | POS | 183362752 | 733451.0 | POS |
| 9 | 10 | 12.0 | 5873 | 23.5 | POS | 40402 | 161.6 | POS | 121607 | 486.4 | POS | 163668880 | 654675.5 | POS |
| 11 | 10 | 12.0 | 4231 | 16.9 | POS | 31486 | 125.9 | POS | 142213 | 568.9 | POS | 162112992 | 648452.0 | POS |

TABLE 7-continued

Milk *Salmonella enterica* Assay

| | | | 5 hr Enrichment | | | 6 hr Enrichment | | | 7 hr Enrichment | | | Overnight Enrichment | | |
|---|---|---|---|---|---|---|---|---|---|---|---|---|---|---|
| | | | 5 hr | 5 hr | 5 hr | 6 hr | 6 hr | 6 hr | 7 hr | 7 hr | 7 hr | | | |
| | 1 mL Sample | | 1 mL | 1 mL | 1 mL | 1 mL | 1 mL | 1 mL | 1 mL | 1 mL | 1 mL | O/N | O/N | O/N |
| Sample | Target Est. Spike | CFU | Conc. RLU | Conc. S/B | Conc. RLU | Conc. RLU | Conc. S/B | Conc. RLU | Conc. RLU | Conc. S/B | Conc. RLU | 1:10 RLU | 1:10 S/B | 1:10 Result |
| 19 | 10 | 12.0 | 2890 | 11.6 | POS | 41600 | 166.4 | POS | 174570 | 698.3 | POS | 196416272 | 785665.1 | POS |
| 21 | 10 | 12.0 | 4090 | 16.4 | POS | 17459 | 69.8 | POS | 67095 | 268.4 | POS | 253096112 | 1012384.4 | POS |
| 29 | 10 | 12.0 | 2650 | 10.6 | POS | 8488 | 34.0 | POS | 38036 | 152.1 | POS | 253975184 | 1015900.7 | POS |
| 6 | 100 | 122 | 36212 | 144.8 | POS | 205489 | 822.0 | POS | 1430167 | 5720.7 | POS | 129592224 | 518368.9 | POS |
| 16 | 100 | 122 | 30119 | 120.5 | POS | 160379 | 641.5 | POS | 859694 | 3438.8 | POS | 247186032 | 988744.1 | POS |
| 26 | 100 | 122 | 33172 | 132.7 | POS | 165894 | 663.6 | POS | 706144 | 2824.6 | POS | 306003808 | 1224015.2 | POS |
| 30 | 100 | 122 | 78723 | 314.9 | POS | 306560 | 1226.2 | POS | 1690050 | 6760.2 | POS | 176066256 | 704265.0 | POS |

We claim:

1. A method for detecting *Salmonella* spp. in a sample comprising:
   incubating a sample comprising powdered infant formula, for 30-120 minutes with a recombinant bacteriophage derived from a *Salmonella*-specific bacteriophage comprising, a genetic construct inserted into a late gene region of the bacteriophage genome, the genetic construct comprising:
   (i) an indicator gene; and
   (ii) a promoter controlling transcription of the indicator gene, wherein the promoter is a bacteriophage late promoter;
   and wherein the indicator gene is not contiguous with a gene encoding a structural bacteriophage protein and does not yield a fusion protein, and wherein expression of the indicator gene results in an indicator protein product; and
   detecting the indicator protein product, wherein positive detection of the indicator protein product indicates that *Salmonella* spp. is present in the sample.

2. The method of claim 1, wherein the method detects as few as 10, 9, 8, 7, 6, 5, 4, 3, 2, or a single bacterium in a sample of a standard size for the food safety industry.

3. The method of claim 1, wherein the sample is incubated with a cocktail composition comprising at least two different types of recombinant bacteriophages, wherein at least one of the recombinant bacteriophages comprises an indicator gene according to claim 1.

4. The method of claim 1, wherein the sample is first incubated in conditions favoring growth for an enrichment period of 24 hours, 23 hours, 22 hours, 21 hours, 20 hours, 19 hours, 18 hours, 17 hours, 16 hours, 15 hours, 14 hours, 13 hours, 12 hours, 11 hours, 10 hours, 9 hours, 8 hours, 7 hours, 6 hours, 5 hours, 4 hours, 3 hours, or 2 hours.

5. The method of claim 3, wherein the total time to results is less than 26 hours, 25 hours, 24 hours, 23 hours, 22 hours, 21 hours, 20 hours, 19 hours, 18 hours, 17 hours, 16 hours, 15 hours, 14 hours, 13 hours, 12 hours, 11 hours, 10 hours, 9 hours 8 hours, 7 hours, 6 hours, 5 hours, 4 hours, 3 hours, or 2 hours.

6. The method of claim 1, wherein the ratio of signal to background generated by detecting the indicator is at least 2.0 or at least 2.5.

* * * * *